(12) United States Patent
Bold et al.

(10) Patent No.: US 8,133,886 B2
(45) Date of Patent: Mar. 13, 2012

(54) HETEROBICYCLIC CARBOXAMIDES AS INHIBITORS FOR KINASES

(75) Inventors: Guido Bold, Gipf-Oberfrick (CH); Andrea Vaupel, Riehen (CH); Carole Pissot Soldermann, Rosenaue (FR); Paul W Manley, Arlesheim (CH)

(73) Assignee: Novartis AG, Basel (CH)

( * ) Notice: Subject to any disclaimer, the term of this patent is extended or adjusted under 35 U.S.C. 154(b) by 447 days.

(21) Appl. No.: 12/446,955

(22) PCT Filed: Mar. 13, 2007

(86) PCT No.: PCT/EP2007/002213
§ 371 (c)(1),
(2), (4) Date: Apr. 23, 2009

(87) PCT Pub. No.: WO2007/104538
PCT Pub. Date: Sep. 20, 2007

(65) Prior Publication Data
US 2010/0029626 A1   Feb. 4, 2010

(30) Foreign Application Priority Data
Mar. 14, 2006 (GB) .................................. 0605120.5

(51) Int. Cl.
C07D 413/12 (2006.01)
C07D 239/30 (2006.01)
A61K 31/495 (2006.01)

(52) U.S. Cl. ............... 514/227.8; 514/256; 514/269; 514/272; 544/60; 544/295; 544/319; 544/320; 544/334

(58) Field of Classification Search ............ 544/60, 544/295, 319, 320, 334; 514/227.8, 256, 514/269, 272
See application file for complete search history.

(56) References Cited

U.S. PATENT DOCUMENTS

| | | | |
|---|---|---|---|
| 6,355,657 B1 | 3/2002 | Osborne et al. | |
| 7,109,219 B2 | 9/2006 | Tsuruoka et al. | |
| 7,253,286 B2 | 8/2007 | Funahashi et al. | |
| 7,468,380 B2 | 12/2008 | Tsuruoka et al. | |
| 2006/0160832 A1 | 7/2006 | Funahashi et al. | |
| 2006/0241115 A1 | 10/2006 | Potashman et al. | |
| 2006/0247259 A1 | 11/2006 | Funahashi et al. | |
| 2008/0287427 A1 | 11/2008 | Bold et al. | |
| 2008/0306058 A1 | 12/2008 | Billich et al. | |

FOREIGN PATENT DOCUMENTS

| | | |
|---|---|---|
| EP | 1415987 B1 | 5/2004 |
| EP | 1522540 A1 | 4/2005 |
| EP | 1568368 A1 | 8/2005 |
| WO | WO 2005/021553 A1 | 3/2005 |
| WO | WO 2005/069906 A2 | 8/2005 |
| WO | WO 2005/070891 A2 | 8/2005 |
| WO | WO 2006/059234 A2 | 6/2006 |
| WO | WO 2007/031265 A2 | 3/2007 |
| WO | WO 2007/104538 A1 | 9/2007 |

OTHER PUBLICATIONS

Chan, Thomas C.K., "Percutaneous Penetration Enhancers: An Update", Proceedings of the 9th Biennal International Conference of Perspectives in Percutaneous Penetration, 2005 pp. 18-22.

Primary Examiner — Deepak Rao
(74) Attorney, Agent, or Firm — John D. Alexander

(57) ABSTRACT

The invention relates to novel compounds of formula (I) and their use in the treatment of the animal or human body, to pharmaceutical compositions comprising a compound of formula (I) and to the use of a compound of formula (I) for the preparation of pharmaceutical compositions for use in the treatment of protein kinase dependent diseases, especially of proliferative diseases, such as in particular tumor diseases.

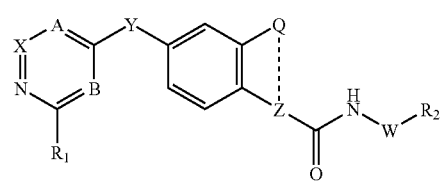

12 Claims, No Drawings

HETEROBICYCLIC CARBOXAMIDES AS INHIBITORS FOR KINASES

This application is the National Stage of Application No. PCT/EP2007/002213, filed on Mar. 13, 2007, which claims benefit under 35 U.S.C. §119(a)-(d) or (f) or 365(b) of EP Application No. 0605120.5, filed Mar. 14, 2006, the contents of which are incorporated herein by reference in their entirety.

The invention relates to bicyclic compounds substituted at both rings of formula I and their use in the treatment of the animal or human body, to pharmaceutical compositions comprising a compound of formula I and to the use of a compound of formula I for the preparation of pharmaceutical compositions for use in the treatment of protein kinase dependent diseases, especially of proliferative diseases, such as in particular tumour diseases.

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive wild-type or mutated PK activity has been observed in many disease states including benign and malignant proliferative disorders. In many cases, it has been possible to treat diseases, such as proliferative disorders, by making use of PK inhibitors.

In view of the large number of protein kinases and the multitude of proliferative and other PK-related diseases, there is an ever-existing need to provide compounds that are useful as PK inhibitors and thus in the treatment of these PK related diseases.

It has now been found that the compounds of formula I show inhibition of a number of protein kinases. The compounds of formula I, described below in more detail, especially show inhibition of one or more of the following protein kinases: EphB4, c-Abl, Bcr-Abl, c-Kit, Raf kinases such as especially B-Raf, the rearranged during transfection (RET) proto-oncogene, Platelet-derived Growth Factor Receptors (PDGF-Rs), Lck, Hck and most especially the Vascular Endothelial Growth Factor Receptors (VEGF-Rs) such as in particular VEGF-R2. The compounds of formula I further also inhibit mutants of said kinases. In view of these activities, the compounds of formula I can be used for the treatment of diseases related to especially aberrant or excessive activity of such types of kinases, especially those mentioned. Structurally related compounds have been described in WO2006/059234.

The invention especially relates to compounds of the formula I,

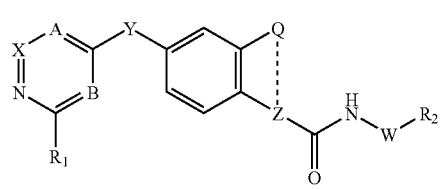

(I)

wherein
$R_1$ is hydroxyl, lower-alkoxy-lower alkyl, lower alkylsulfonylamino, amino-lower alkylamino, N-mono- or N,N-di-(lower alkyl)amino-lower alkylamino, N-mono- or N,N-di-(lower alkyl)amino-carbonyl-amino, piperazinyl-lower alkylamino, N-lower alkylpiperazinyl-lower alkylamino, hydrazino, mono-, di- or tri-(lower-alkyl)-substituted hydrazino, $R_2$ is phenyl substituted by a substituent selected from the group consisting of phenoxy, piperazinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

or is phenyl substituted by one or two moieties independently selected from lower alkyl, $C_3$-$C_8$-cycloalkyl, halo, halo-lower alkyl, halo-lower alkoxy or by lower alkoxy, or is 2H-pyrazolyl substituted by halophenyl and lower alkyl;

or is 2H-pyrazolyl substituted by halophenyl and lower alkyl; or wherein $R_1$ is halo, especially chloro, amino, lower alkylamino, lower alkanoylamino, lower alkoxycarbonylamino, $C_{3-8}$cycloalkylcarbonyl amino or hydroxyl-lower alkyl and $R_2$ is phenyl substituted by a substituent selected from the group consisting of phenoxy, piperazinyl-lower alkyl, lower-alkylpiperazinyl, lower-alkylpiperazinyl-lower alkyl, $C_3$-$C_8$-cycloalkyl-piperazinyl-lower alkyl, phenyl lower-alkyl piperazinyl, piperidinyl-lower alkyl, lower-alkylpiperidinyl-lower alkyl, amino piperidinyl, lower alkoxycarbonylamino piperidinyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl, N-mono- or N,N-di-lower alkylaminopyrrolidinyl lower alkyl, 1,1-dioxido-4-thiomorpholinyl, and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

A, B and X are independently selected from C($R_3$) or N, with the proviso that not more than one of A, B and X is N;
$R_3$ is lower alkyl, halo or hydrogen;
Y is O, S, S(O), S(O)$_2$, CH$_2$ or CH$_2$—CH$_2$;
and
Q-Z is either
O—CH$_2$—N (wherein O is in the place of Q and N in the place of Z), or
CH=CH—N=C wherein the left CH is in the place of Q and the right C is at the place of Z; or
CH=CH—CH=C wherein the left CH is in the place of Q and the right C is in the place of Z in formula I, respectively;
W is absent or is lower alkylene, especially CH$_2$, CH$_2$—CH$_2$ or CH$_2$—CH$_2$—CH$_2$;
with the proviso that
if one of A, B and X is N, and Y is O, then in addition or alternatively a compound of formula I wherein $R_1$ is hydroxyl-lower alkyl and at the same time
$R_2$ is phenyl that is substituted by one or two moieties independently selected from the group consisting of lower alkyl, $C_3$-$C_8$-cycloalkyl, halo, halo lower alkyl, lower alkoxy, phenoxy, piperazinyl-lower alkyl, lower-alkylpiperazinyl-lower alkyl and halo-lower alkoxy,
while the other symbols Q-Z and W are as defined above, is included;
and with the proviso that
if one of A, B and X is N and Y is $CH_2$, then in addition or alternatively a compound of the formula I wherein
$R_1$ is halo, amino, lower alkylamino, lower alkanoylamino or lower alkoxycarbonylamino and
$R_2$ is phenyl that is substituted by two moieties independently selected from halo, halo-lower alkyl, piperazinyl-lower alkyl and lower-alkyl-piperazinyl-lower alkyl,
while the other symbols Q-Z and W are as defined above, is included;
and with the proviso, that
if X is CH, A is CH, B is N, Y is O and W and Q-Z are as defined above, then in addition or alternatively a compound of the formula I wherein
$R_1$ is lower alkoxycarbonyl or lower alkanoyl and
$R_2$ is phenyl substituted in 4-position by halo and in 3-position by halo-lower alkyl;
a tautomer and/or a (preferably pharmaceutically acceptable) salt thereof.

The present invention also relates to a method of treating a kinase dependent and/or proliferative disease comprising administering a compound of the formula I to a warm-blooded animal, especially a human, and the use of a compound of the formula I, especially for treating a kinase dependent disease or disorder. The present invention also relates to pharmaceutical preparations comprising a compound of the formula I, especially for the treatment of a kinase dependent disease or disorder, a process for the manufacture of a compound of the formula I, and novel starting materials and intermediates for their manufacture. The present invention also relates to the use of a compound of formula I in the manufacture of a pharmaceutical preparation for the treatment of a kinase dependent disease.

The general terms used hereinbefore and hereinafter preferably have, within this disclosure, the following meanings, unless otherwise indicated (where preferred embodiments can be defined by replacing one or more up to all general expressions or symbols with (a) more specific or more preferred definition(s) given herein).

In formula I the following significances are preferred independently, collectively or in any combination or sub-combination.

The term "lower" defines a moiety with up to and including maximally 7, especially up to and including maximally 4, carbon atoms, said moiety being branched or straight-chained. Lower alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Lower-alkoxy-lower alkyl is preferably methoxymethyl.

Lower alkylsulfonylamino is preferably methylsulfonylamino ($H_3C$—$S(=O)_2$—NH—).

N-mono- or (the preferred) N,N-di-(lower alkyl)amino-lower alkylamino is preferably 2-(N,N-dimethylamino)ethylamino or 3-(N,N-dimethylamino)propylamino.

N-Mono- or N,N-di-(lower alkyl)aminocarbonyl-amino is preferably methylaminocarbonyl-amino.

Piperazinyl-lower alkylamino or N-lower alkylpiperazinyl-lower alkylamino is preferably piperazino-methyl- or 3-piperazino-propylamino which is unsubstituted or preferably substituted at the nitrogen in 4-position by methyl or ethyl.

$C_3$-$C_8$-Cycloalkyl-piperazinyl-lower alkyl is preferably 4-cyclopropyl-piperazin-1-ylmethyl.

Hydrazino is preferably unsubstituted.

In phenyl that is substituted by a substituent selected from the group consisting of phenoxy, piperazinyl-lower alkyl, lower-alkylpiperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy, the substituents are preferably bound in the 3- and/or the 4-position (meta and/or para position). Piperazinyl-lower alkyl is preferably piperazinomethyl.

Lower-alkylpiperazinyl-lower alkyl is preferably 4-methyl- or 4-ethyl-piperazino-methyl.

Piperidinyl-lower alkyl is preferably piperidin-4-yl-methyl, the more preferred lower-alkylpiperidinyl-lower alkyl is preferably 1-methyl-piperidin-4-ylmethyl.

Piperidinyliden-lower alkyl is preferably piperidin-4-yliden-methyl, the more preferred lower-alkylpiperidinyliden-lower alkyl is preferably 1-methyl-piperidin-4-ylidenmethyl.

Piperidinyloxy is preferably piperidin-4-yloxy, the more preferred lower alkylpiperidinyloxy is preferably 1-methyl-piperidin-4-yloxy.

Pyrrolidinyl is preferably pyrrolidino, amino-pyrrolidinyl is preferably 3-aminopyrrolidin and the more preferred N-mono- or especially N,N-di-lower alkylaminopyrrolidinyl is preferably 3-(N-mono- or preferably N,N-dimethylamino)-pyrrolidino.

9-Lower alkyl-3,9-diazabicyclo[3.3.1]non-3-yl-lower alkyl is preferably 9-methyl-3,9-diazabicyclo[3.3.1]non-3-ylmethyl.

$C_3$-$C_8$-cycloalkyl is preferably cyclopropyl.

Halo is preferably fluoro, chloro, bromo or iodo, more preferably fluoro or chloro.

In halo-lower alkyl, one or more halo atoms, especially fluoro, can be present—preferred is trifluoromethyl or difluoromethyl.

In halo-lower alkoxy, one or more halo atoms, especially fluoro, can be present—preferred is trifluoromethoxy.

In 2H-pyrazolyl that is unsubstituted or substituted by lower alkyl and by one or two moieties independently selected from lower alkoxyphenyl and lower alkoxyphenylphenyl, 2H-pyrazolyl is preferably 2H-pyrazol-3-yl and the lower alkyl (preferably tert-butyl) is preferably bound to the 2H-pyrazolyl in 5-position, the lower alkoxyphenyl (preferably 4-methoxyphenyl) or the lower alkoxyphenylphenyl (preferably 4-(4-methoxyphenyl)-phenyl) in 2-position (at the N).

In phenyl that is substituted by one or two moieties independently selected from lower alkyl (preferably methyl), $C_3$-$C_8$-cycloalkyl (preferably cyclopropyl), halo (preferably chloro or fluoro), halo-lower alkyl (preferably trifluoromethyl), halo-lower alkoxy (preferably trifluoromethoxy) or by lower alkoxy (preferably methoxy), the substitutents are preferably bound in the 3- and/or the 4-position of the phenyl (meta or para position).

In 2H-pyrazolyl substituted by halophenyl (preferably 4-fluorophenyl) and lower alkyl (preferably tert-butyl), 2H-pyrazolyl is preferably 2H-pyrazol-3-yl and the lower alkyl is preferably bound to the 2H-pyrazolyl in 5-position, the halophenyl in 2-position (at the N).

Lower alkylamino is preferably methylamino.

Lower alkanoylamino is preferably acetylamino.

Lower alkoxycarbonylamino is preferably methoxycarbonylamino, isobutoxycarbonylamino or tert-butoxycarbonylamino.

Hydroxyl-lower alkyl or lower alkanoyl is preferably hydroxymethyl.

Preferably, one of A, B and X is N, the others are CH. More preferably, one of A and B is N, the other and X are CH.

Y is preferably O, S, S(O), $S(O)_2$ or $CH_2$, most preferred O or $CH_2$.

W is preferably absent.

Preferred is a compound of the formula IA,

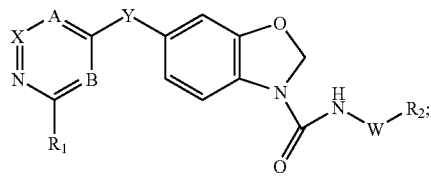

a compound of the formula IB,

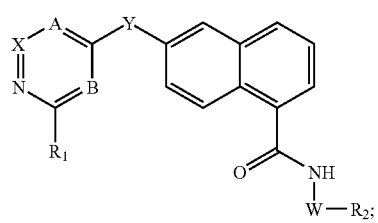

a compound of the formula IC,

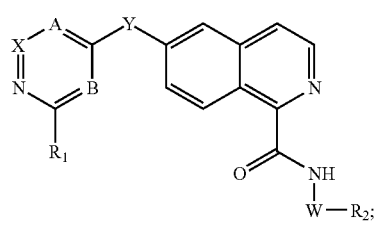

where $R_1$, $R_2$, X, A, B, Y and W in the formulae IA to IC (all of which fall under formula I) are as defined for a compound of the formula I, or in each case or a tautomer thereof, and/or pharmaceutically acceptable salt thereof.

Preferred is a compound of the formula IA,

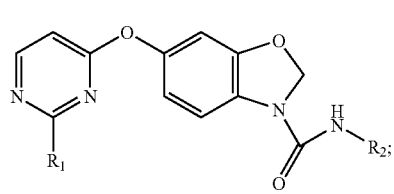

wherein R1 is halogen or lower alkylamino, and R2 is phenyl which is di-substituted by halogen and halo lower alkyl or in each case or a tautomer thereof, and/or pharmaceutically acceptable salt thereof.

In one embodiment, the invention pertains to a compound of formula IA wherein R1 is chloro, or methyl amino and R2 is phenyl which is disubstituted by an halogen being chloro or fluoro and trifluoromethyl.

Preferred is a compound of the formula IB,

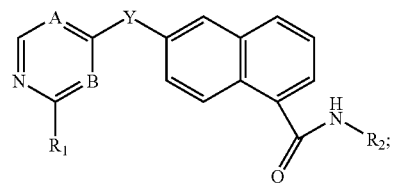

wherein R1 is hydroxyl, halogen, amino, lower alkyl amino, lower alkoxy carbonyl amino, lower alkyl carbonylamino, lower alkoxycarbonyl, lower alkylsulfonylamino, N-mono-lower alkylaminocarbonylamino, lower alkoxy lower alkyl, hydroxyl lower alkyl, N,N-di-lower alkylamino-lower alkylamino, N-lower alkylpiperazinyl-lower alkylamino, Y is C or O, A and B are independently selected from CH or N, with the proviso that not more than one of A and B is N;

R2 is phenyl which is monosubstituted by halo-lower alkyl, $C_{3-8}$cycloalkyl, lower alkyl, phenoxy, lower alkylpiperazinyl, halo-lower alkoxy, lower alkylpiperazinyl lower alkyl;

R2 is phenyl which is disubstituted by lower alkyl, or by lower alkoxy or by one substituent being halo lower alkyl and the second substituent is selected from the group consisting of halogen, lower alkylpiperazinyl lower alkyl, lower alkyl, lower alkyl piperidinyl oxy, lower alkyl piperidinyl lower alkyl, 9-lower alkyl-3,9-diazabicyclo[3.3.1]non-3-yl-lower alkyl, N,N-di-lower alkylaminopyrrolidinyl, N,N-di-lower alkylaminopyrrolidinyl lower alkyl, lower-alkylpiperidinyliden-lower alkyl, 1,1-dioxothiomorpholinyl, lower alkyl imidazolyl, lower alkoxy carbonyl amino piperidinyl, and amino piperidinyl;

R2 is pyrazolyl which is disubstituted by one lower alkyl substituent and one substituent selected from lower alkoxy phenyl or halo phenyl. (Ex 19-22).

Preferred is a compound of the formula IB wherein when R2 is disubstituted phenyl, one of the substituent is trifluoromethyl.

Preferred is a compound of the formula IC,

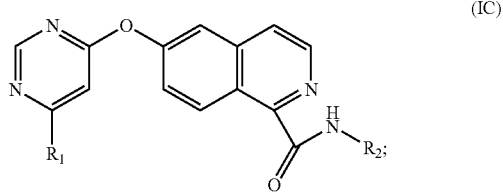

(IC)

wherein R1 is lower-alkylcarbonylamino, and R2 is 2H-pyrazolyl that is substituted by lower alkyl and by lower alkoxyphenyl or in each case or a tautomer thereof, and/or pharmaceutically acceptable salt thereof.

Preferred is also a compound of the formula I wherein
$R_1$ is hydroxyl, lower-alkoxy-lower alkyl, lower alkylsulfonylamino, amino-lower alkylamino, N-mono- or N,N-di-(lower alkyl)amino-lower alkylamino, N-mono- or N,N-di-(lower alkyl)aminocarbonyl-amino, piperazinyl-lower alkylamino, N-lower alkylpiperazinyl-lower alkylamino, hydrazino, mono-, di- or tri-(lower-alkyl)-substituted hydrazine;

$R_2$ is phenyl substituted by a substituent selected from the group consisting of phenoxy, piperazinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

and A, B, X, Y, Q-Z, W and $R_2$ are as defined in claim 1;

a tautomer and/or a (preferably pharmaceutically acceptable) salt thereof.

Preferred is also a compound of the formula I wherein
$R_1$ is hydroxyl, lower alkoxy-lower alkyl, amino-lower alkylamino, or N-mono- or N,N-di-(lower alkyl)amino-lower alkylamino, and $R_2$ is phenyl substituted by one or two moieties independently selected from lower alkyl, $C_3$-$C_8$-cycloalkyl, halo, halo-lower alkyl, halo-lower alkoxy or by lower alkoxy, or is 2H-pyrazolyl substituted by halophenyl and lower alkyl.

Preferred is also a compound of the formula I wherein
$R_1$ is halo, piperazinyl-lower alkylamino or N-lower alkylpiperazinyl-lower alkylamino, and $R_2$ is 2H-pyrazolyl substituted by halophenyl and lower alkyl;

Preferred is also a compound of the formula I wherein
$R_1$ is halo, especially chloro, amino, lower alkylamino, lower alkanoylamino, lower alkoxycarbonylamino or hydroxyl-lower alkyl and $R_2$ is phenyl substituted by a substituent selected from the group consisting of phenoxy, piperazinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

Preferred is also a compound of the formula I wherein
$R_1$ is hydroxyl-lower alkyl or preferably lower alkoxy-lower alkyl;

$R_2$ is phenyl that is substituted by one or two moieties independently selected from the group consisting of lower alkyl, $C_3$-$C_8$-cycloalkyl, halo, halo lower alkyl, lower alkoxy, phenoxy, piperazinyl-lower alkyl, lower-alkylpiperazinyl-lower alkyl and halo-lower alkoxy, one of A, B and X is N, the others are $CH_2$; and Y is O.

Preferred is also a compound of the formula I wherein
$R_1$ is halo, amino, lower alkylamino, lower alkanoylamino or lower alkoxycarbonylamino and $R_2$ is phenyl that is substituted by two moieties independently selected from halo, halo-lower alkyl, piperazinyl-lower alkyl and lower-alkyl-piperazinyl-lower alkyl, one of A, B and X is N and the others are $CH_2$, and Y is $CH_2$.

Preferred is also a compound of the formula I wherein
$R_1$ is lower alkoxy-lower alkyl, $R_2$ is phenyl substituted by a substituent selected from the group consisting of phenoxy, piperazinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

or is phenyl substituted by one or two moieties independently selected from lower alkyl, $C_3$-$C_8$-cycloalkyl, halo, halo-lower alkyl, halo-lower alkoxy or by lower alkoxy, or is 2H-pyrazolyl substituted by halophenyl and lower alkyl;

or is 2H-pyrazolyl substituted by halophenyl and lower alkyl.

Preferred is also a compound of the formula I wherein
$R_1$ is lower alkoxycarbonyl or lower alkanoyl;

$R_2$ is phenyl substituted in 4-position by halo and in 3-position by halo-lower alkyl;

X is CH;

B is N;

Y is O.

In another preferred embodiment the present invention relates to a compound of the formula I,

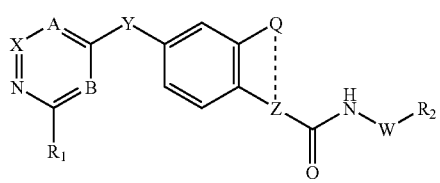

wherein R₁ is hydroxyl, lower-alkoxy-lower alkyl, lower alkylsulfonylamino, amino-lower alkylamino, N-mono- or N,N-di-(lower alkyl)amino-lower alkylamino, N-mono- or N,N-di-(lower alkyl)aminocarbonyl-amino, piperazinyl-lower alkylamino, N-lower alkylpiperazinyl-lower alkylamino, hydrazino, mono-, di- or tri-(lower-alkyl)-substituted hydrazino,
R₂ is phenyl substituted by a substituent selected from the group consisting of phenoxy, piperazinyl-lower alkyl, lower-alkylpiperazinyl-lower alkyl, C₃-C₈-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, C₃-C₈-cycloalkyl, halo, halo-lower alkyl, halo-lower alkoxy and lower alkoxy;
or is 2H-pyrazolyl that is unsubstituted or substituted by lower alkyl and by one or two moieties independently selected from lower alkoxyphenyl and lower alkoxyphenylphenyl;
or is phenyl substituted by one or two moieties independently selected from lower alkyl, C₃-C₈-cycloalkyl, halo, halo-lower alkyl, halo-lower alkoxy or by lower alkoxy, or is 2H-pyrazolyl substituted by halophenyl and lower alkyl;
or is 2H-pyrazolyl substituted by halophenyl and lower alkyl;
or wherein
R₁ is halo, especially chloro, amino, lower alkylamino, lower alkanoylamino, lower alkoxycarbonylamino or hydroxyl-lower alkyl and
R₂ is phenyl substituted by a substituent selected from the group consisting of phenoxy, piperazinyl-lower alkyl, lower-alkylpiperazinyl-lower alkyl, C₃-C₈-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, C₃-C₈-cycloalkyl, halo, halo-lower alkyl, halo-lower alkoxy and lower alkoxy;
or is 2H-pyrazolyl that is unsubstituted or substituted by lower alkyl and by one or two moieties independently selected from lower alkoxyphenyl and lower alkoxyphenylphenyl;
A, B and X are independently selected from C(R₃) or N, with the proviso that not more than one of A, B and X is N;
R₃ is lower alkyl, halo or hydrogen;
Y is O, S, S(O), S(O)₂, CH₂ or CH₂—CH₂;
and
Q-Z is either
O—CH₂—N (wherein O is in the place of Q and N in the place of Z), or
CH═CH—N═C wherein the left CH is in the place of Q and the right C is at the place of Z; or
CH═CH—CH═C wherein the left CH is in the place of Q and the right C is in the place of Z in formula I, respectively;
W is absent or is lower alkylene, especially CH₂, CH₂—CH₂ or CH₂—CH₂—CH₂;
with the proviso that if one of A, B and X is N, and Y is O, then in addition or alternatively a compound of formula I wherein R₁ is hydroxyl-lower alkyl and at the same time
R₂ is phenyl that is substituted by one or two moieties independently selected from the group consisting of lower alkyl, C₃-C₈-cycloalkyl, halo, halo lower alkyl, lower alkoxy, phenoxy, piperazinyl-lower alkyl, lower-alkylpiperazinyl-lower alkyl and halo-lower alkoxy,
while the other symbols Q-Z and W are as defined above, is included;
and with the proviso that if one of A, B and X is N and Y is CH₂, then in addition or alternatively a compound of the formula I wherein
R₁ is halo, amino, lower alkylamino, lower alkanoylamino or lower alkoxycarbonylamino and
R₂ is phenyl that is substituted by two moieties independently selected from halo, halo-lower alkyl, piperazinyl-lower alkyl and lower-alkyl-piperazinyl-lower alkyl,
while the other symbols Q-Z and W are as defined above, is included;
and with the proviso, that if X is CH, A is CH, B is N, Y is O and W and Q-Z are as defined above, then in addition or alternatively a compound of the formula I wherein
R₁ is lower alkoxycarbonyl or lower alkanoyl and
R₂ is phenyl substituted in 4-position by halo and in 3-position by halo-lower alkyl;
a tautomer and/or a (preferably pharmaceutically acceptable) salt thereof.

Where the plural form is used for compounds, salts, pharmaceutical compositions, diseases and the like, this is intended to mean also a single compound, salt, or the like.

In view of the close relationship between the compounds of formula I in free form and in the form of their salts, including those salts that can be used as intermediates, for example in the purification or identification of the compounds of formula I, tautomers or tautomeric mixtures and their salts, any reference hereinbefore and hereinafter to these compounds is to be understood as referring also to the corresponding tautomers of these compounds, tautomeric mixtures of these compounds, N-oxides of these compounds, or salts of any of these, as appropriate and expedient and if not mentioned otherwise. Tautomers can, e.g., be present in cases where amino or hydroxy are bound to carbon atoms that are bound to adjacent atoms by double bonds (e.g. keto-enol or imine-enamine tautomerism).

Asymmetric carbon atoms of a compound of formula I that are optionally present may exist in the (R), (S) or (R,S) configuration, preferably in the (R) or (S) configuration. Substituents at a double bond or a ring may be present in cis- (═Z-) or trans (═E-) form. The compounds may thus be present as mixtures of isomers or preferably as pure isomers.

Salts are preferably the pharmaceutically acceptable salts of the compounds of formula I.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The terms "treatment" or "therapy" refer to the prophylactic or preferably therapeutic (including but not limited to palliative, curing, symptom-alleviating, symptom-reducing, kinase-regulating and/or kinase-inhibiting) treatment of said diseases, especially of the diseases mentioned below.

Where subsequently or above the term "use" is mentioned (as verb or noun) (relating to the use of a compound of the formula I or a pharmaceutically acceptable salt thereof), this includes any one or more of the following embodiments of the invention, respectively: the use in the treatment of a protein kinase dependent disease, the use for the manufacture of pharmaceutical compositions for use in the treatment of a protein kinase dependent disease, methods of use of one or more compounds of the formula I in the treatment of a protein kinase dependent disease, the use of pharmaceutical preparations comprising one or more compounds of the formula I for the treatment of a protein kinase dependent disease, and one or more compounds of the formula I for use in the treatment of a protein kinase dependent disease, as appropriate and expedient and if not stated otherwise. In particular, diseases to be treated and are thus preferred for "use" of a compound of formula I are selected from protein kinase dependent ("dependent" meaning also "supported", not only "solely dependent") diseases mentioned herein, especially proliferative diseases mentioned herein, more especially any one or more of these or other diseases that depend on one or more of c-Abl, Bcr-Abl, c-Kit, Raf kinases such as especially B-Raf, the rearranged during transfection (RET) proto-oncogene, Platelet-derived Growth Factor Receptors (PDGF-Rs), Lck, Hck and most especially the Vascular Endothelial Growth Factor Receptors (VEGF-Rs) such as in particular VEGF-R2, or a mutant of any one or more of these, and a compound of the formula I can therefore be used in the treatment of a kinase dependent disease, especially a disease depending on one or more of the kinases mentioned above and below, where (especially in the case of aberrantly highly-expressed, constitutively activated and/or mutated kinases) said kinase-dependent disease is dependent on the activity of one or more of the said kinases or the pathways they are involved.

The compounds of formula I have valuable pharmacological properties and are useful in the treatment of protein kinase dependent diseases, for example as drugs to treat proliferative diseases.

The efficacy of the compounds of formula I as inhibitors of c-Abl protein tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 µL): c-Abl kinase (50 ng), 20 mM Tris.HCl, pH 7.5, 10 mM $MgCl_2$, 10 µM $Na_3VO_4$, 1 mM DTT and 0.06 µCi/assay [$\gamma\ ^{33}P$]-ATP (5 µM ATP) using 30 µg/ml poly-Ala, Glu, Lys, Tyr-6:2:5:1 (Poly-AEKY, Sigma P1152) in the presence of 1% DMSO. Reactions are terminated by adding 10 µL of 250 mM EDTA and 30 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). Using this test system, the compounds of formula I show $IC_{50}$ values of inhibition in the range of 0.001 to 100 µM, usually between 0.05 and 5 µM.

Bcr-Abl inhibition can be determined by a capture ELISA as follows: The murine myeloid progenitor cell line 32Dcl3 transfected with the p210 Bcr-Abl expression vector pGDp210Bcr/Abl (32D-bcr/abl) is obtained from J Griffin (Bazzoni et al., J. Clin Invest. 98, 521-8 (1996); Zhao et al., Blood 90, 4687-9 (1997)). The cells express the fusion bcr-abl protein with a constitutively active abl kinase and proliferate growth factor-independent. The cells are expanded in RPMI 1640 (AMIMED; cat#1-41F01), 10% fetal calf serum, 2 mM glutamine (Gibco) ("complete medium"), and a working stock is prepared by freezing aliquots of $2\times10^6$ cells per vial in freezing medium (95% fetal calf serum, 5% dimethylsulfoxide (SIGMA, D-2650). After thawing, the cells are used during maximally 10-12 passages for the experiments. The antibody anti-abl SH3 domain cat. #06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. #03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (STI571) (marketed as Gleevece® or Glivec®, Novartis), is used. A stock solution of 10 mM is prepared in DMSO and stored at −20° C. For the cellular assays, the stock solution is diluted in complete medium in two steps (1:100 and 1:10) to yield a starting concentration of 10 µM followed by preparation of serial threefold dilutions in complete medium. No solubility problems are encountered using this procedure. The test compounds of formula I are treated analogously. For the assay, 200,000 32D-bcr/abl cells in 50 µl are seeded per well in 96 well round bottom tissue culture plates. 50 µl per well of serial threefold dilutions of the test compound are added to the cells in triplicates. The final concentration of the test compound range e.g. from 5 µM down to 0.01 µM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 µg/ml aprotinin and 80 µg/ml leupeptin) and either used immediately for the ELISA or stored frozen at −20° C. until usage. The anti-abl SH3 domain antibody is coated at 200 ng in 50 µl PBS per well to black ELISA plates (Packard HTRF-96 black plates; 6005207) overnight at 4° C. After washing 3× with 200 µl/well PBS containing 0.05% Tween 20 (PBST) and 0.5% TopBlock (Juro, Cat. # TB 232010), residual protein binding sites are blocked with 200 µl/well PBST, 3% TopBlock for 4 h at room temperature, followed by incubation with 50 µl lysates of untreated or test compound-treated cells (20 µg total protein per well) for 3-4 h at 4° C. After 3× washing, 50 µl/well PY20(AP) (Zymed) diluted to 0.5 µg/ml in blocking buffer is added and incubated over-night (4° C.). For all incubation steps, the plates are covered with plate sealers (Costar, cat. #3095). Finally, the plates are washed another three times with washing buffer and once with deionized water before addition of 90 µl/well of the AP substrate CPD-Star RTU with Emerald II. The plates now sealed with Packard Top Seal™-A plate sealers (cat. #6005185) are incubated for 45 min at room temperature in the dark and luminescence is quantified by measuring counts per second (CPS) with a Packard Top Count Microplate Scintillation Counter (Top Count). For the final optimized version of the ELISA, 50 µl of the lysates of the cells grown, treated and lysed in 96 well tissue culture plates, are transferred directly from these plates to the ELISA plates that are precoated with 50 ng/well of the rabbit polyclonal ant-abl-SH3 domain AB 06-466 from Upstate. The concentration of the anti-phosphotyrosine AB PY20 (AP) can be reduced to 0.2 µg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the $IC_{50}$ are determined from the dose response curves by graphical inter- or extrapolation. The compounds of formula I here show $IC_{50}$ values in the range from 10 nM to 20 µM.

The inhibition of phosphorylation of Bcr-Abl or Bcr-Abl T315I can be determined by the same capture ELISA format as follows: The murine myeloid progenitor cell line 32Dcl3 transfected with the p210 Bcr-Abl expression vector pGDp210Bcr/Abl (32D-bcr/abl) is obtained from J Griffin (Bazzoni et al., J. Clin Invest. 98, 521-8 (1996); Zhao et al., Blood 90, 4687-9 (1997)). The cells express the fusion bcr-abl protein with a constitutively active abl kinase and proliferate growth factor-independent. The murine myeloid progenitor cell line Ba/F3 transfected with the p210 Bcr-Abl T315I expression vector pCl-neo (Mammalian expression Vector; Promega (#E1841) is obtained from J Griffin (Weisberg et al Blood 2006 Oct. 26 [Epub ahead of print]. The cells express the fusion bcr-abl protein carrying the T315I mutation within the constitutively active abl kinase and proliferate growth factor-independent. The cells are expanded in RPMI 1640 (AMIMED; cat #1-41F01), 10% fetal calf serum, 2 mM glutamine (Gibco) ("complete medium"), and a working stock is prepared by freezing aliquots of $2 \times 10^6$ cells per vial in freezing medium (95% fetal calf serum, 5% dimethylsulfoxide (SIGMA, D-2650). After thawing, the cells are used during maximally 10-12 passages for the experiments. The antibody anti-abl SH3 domain cat. #06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. #03-7722) is used. As comparison and reference compound, NVP-AMN107 or nilotinib, (Novartis), is used. A stock solution of 10 mM is prepared in DMSO and stored at −20° C. For the cellular assays, the stock solution is diluted in complete medium to yield a starting concentration of 20 or 6 µM followed by preparation of serial threefold dilutions in complete medium. No solubility problems are encountered using this procedure. The test compounds of formula I are treated analogously. For the assay, 200,000 32D-bcr/abl or Ba/F3 bcr/abl T315I cells in 50 µl are seeded per well in 96 well round bottom tissue culture plates. 50 µl per well of serial threefold dilutions of the test compound are added to the cells in triplicates. The final concentration of the test compound range e.g. from 10 µM down to 0.01 µM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 µg/ml aprotinin and 80 µg/ml leupeptin) and either used immediately for the ELISA or stored frozen at −20° C. until usage. The anti-abl SH3 domain antibody is coated at 200 ng in 50 µl PBS per well to black ELISA plates (Packard HTRF-96 black plates; 6005207) overnight at 4° C. After washing 3× with 200 µl/well PBS containing 0.05% Tween 20 (PBST) and 0.5% TopBlock (Juro, Cat. # TB 232010), residual protein binding sites are blocked with 200 µl/well PBST, 3% TopBlock for 4 h at room temperature, followed by incubation with 50 µl lysates of untreated or test compound-treated cells (20 µg total protein per well) for 3-4 h at 4° C. After 3× washing, 50 µl/well PY20(AP) (Zymed) diluted to 0.5 µg/ml in blocking buffer is added and incubated overnight (4° C.). For all incubation steps, the plates are covered with plate sealers (Costar, cat. #3095). Finally, the plates are washed another three times with washing buffer and once with deionized water before addition of 90 µl/well of the AP substrate CPDStar RTU with Emerald II. The plates now sealed with Packard Top Seal™-A plate sealers (cat. #6005185) are incubated for 45 min at room temperature in the dark and luminescence is quantified by measuring counts per second (CPS) with a Packard Top Count Microplate Scintillation Counter (Top Count). For the final optimized version of the ELISA, 50 µl of the lysates of the cells grown, treated and lysed in 96 well tissue culture plates, are transferred directly from these plates to the ELISA plates that are pre-coated with 50 ng/well of the rabbit polyclonal ant-abl-SH3 domain AB 06-466 from Upstate. The concentration of the anti-phosphotyrosine AB PY20 (AP) can be reduced to 0.2 µg/ml. Washing, blocking and incubation with the luminescent substrate are as above. The quantification is achieved as follows: The difference between the ELISA readout (CPS) obtained for with the lysates of the untreated cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the $IC_{50}$ are determined from the dose response curves by graphical inter- or extrapolation. The compounds of formula I here show $IC_{50}$ values in the range from 20 nM to 10 µM.

The efficacy of the compounds of formula I as inhibitors of c-Kit and PDGF-R tyrosine kinase activity can be demonstrated as follows:
BaF3-Tel-PDGFRbeta and BaF3-KitD816V are BaF3 murine proB-cell lymphoma cell derivatives [the BaF3 cell line is available from the German Collection of Microorganisms and Cell Cultures (DSMZ), Braunschweig, Germany] that have been rendered IL-3-independent by stable transduction with Tel-fusion-activated PDGFβ-R wild-type (Golub T. R. et al., Cell 77(2): 307-316, 1994) or D816V-mutation-activated c-kit, respectively. Cells are cultured in RPMI-1640 (Animed #1-14F01-I) supplemented with 2% L-glutamine (Animed #5-10K50-H) and 10% fetal calf serum (FCS, Animed #2-01F16-I). Wild-type, untransfected BaF3 cells are maintained in above medium plus 10 U/ml IL-3 (mouse Interleukin-3, Roche #1380745). Cells are diluted in fresh medium to a final density of $3 \times 10^5$ cells per ml and 50 µl aliquots seeded into 96-well plates ($1.5 \times 10^4$ cells per well). 50 µl 2× compound solutions are added. As internal control, the kinase inhibitor PKC412 is routinely used. Control cells treated with DMSO (0.1% final concentration) serve as growth reference (set as 100% growth). In addition, a plate blank value is routinely determined in a well containing only 100 µl of medium and no cells. $IC_{50}$ determinations are performed based on eight 3-fold serial dilutions of the test compound, starting at 10 µM. Following incubation of the cells for 48 h at 37° C. and 5% $CO_2$, the effect of inhibitors on cell viability is assessed by the resazurin sodium salt dye reduction assay (commercially known as AlamarBlue assay) basically as previously described (O'Brien J. et al., Eur. J. Biochem. 267: 5421-5426, 2000). 10 µl of AlamarBlue is added per well and the plates incubated for 6 h at 37° C. and 5% $CO_2$. Thereafter, fluorescence is measured using a Gemini 96-well plate reader (Molecular Devices) with the following settings: Excitation 544 nm and Emission 590 nm. Acquired raw data are exported to Excel-file format. For data analysis, the plate blank value is subtracted from all data points. The anti-proliferative effect of a compound by the AlamarBlue read-out was then calculated as percentage of the value of the control cells set as 100%. $IC_{50}$ values are determined using XLfit software program. The compounds of formula I show an $IC_{50}$ for c-Kit and PDGFβ-R in the range of 0.001 to 20 µM, especially between 0.001 and 0.1 µM.

Active Raf kinases, such as active B-Raf protein, of human sequence are purified from insect cells using the baculoviral expression system. Raf inhibition is tested in 96-well microplates coated with IκB-α and blocked with Superblock. The phosphorylation of IκB-α at Serine 36 is detected using a phospho-IκB-α specific antibody (Cell Signaling #9246), an anti-mouse IgG alkaline phosphatase conjugated secondary antibody (Pierce #31320), and an alkaline phosphatase substrate, ATTOPHOS (Promega, #S101).

RET kinase inhibition is determined as follows:
Cloning and expression: The baculovirus donor vector pFB-GSTX3 is used to generate a recombinant baculovirus that expresses the amino acid region 658-1072 (Swiss prot No. Q9BTB0) of the cytoplasmic kinase domain of human RET-Men2A which corresponds to the wild-type kinase domain of RET (wtRET) and RET-Men2B, which differs from the wtRET by the activating mutation in the activation loop M918T. The coding sequence for the cytoplasmic domain of wtRET is amplified by PCR from a cDNA library using specific primers. RET-Men2B is generated through site-directed mutagenesis resulting in the M918T mutation. The amplified DNA fragments and the pFB-GSTX3 vector are made compatible for ligation by digestion with SalI and KpnI. Ligation of these DNA fragments results in the baculovirus donor plasmids pFB-GX3-RET-Men2A and pFB-GX3-RET-Men2B, respectively.

Production of virus: The baculovirus donor plasmids containing the kinase domains are transfected into the DH10Bac cell line (GIBCO) and the transfected cells are plated on selective agar plates. Colonies without insertion of the fusion sequence into the viral genome (carried by the bacteria) are blue. Single, white colonies are picked and viral DNA (bacmid) is isolated from the bacteria by standard plasmid purification procedures. Sf9 cells or Sf21 cells (American Type Culture Collection) are then transfected in 25 $cm^2$ flasks with the viral DNA using Cellfectin reagent.

Protein expression in Sf9 cells: Virus-containing media is collected from the transfected cell culture and used for infection to increase its titer. Virus-containing media obtained after two rounds of infection is used for large-scale protein expression. For large-scale protein expression 100 $cm^2$ round tissue culture plates are seeded with $5 \times 10^7$ cells/plate and infected with 1 ml of virus-containing media (approximately 5 MOIs). After 3 days, the cells are scraped off the plate and centrifuged at 500 rpm for 5 minutes. Cell pellets from 10-20, 100 $cm^2$ plates are re-suspended in 50 ml of ice-cold lysis buffer (25 mM Tris-HCl, pH 7.5, 2 mM EDTA, 1% NP-40, 1 mM DTT, 1 mM PMSF). The cells are stirred on ice for 15 minutes and then centrifuged at 5,000 rpms for 20 minutes.

Purification of GST-tagged proteins: The centrifuged cell lysate is loaded onto a 2 ml glutathione-sepharose column (Pharmacia) and washed 3× with 10 ml of 25 mM Tris-HCl, pH 7.5, 2 mM EDTA, 1 mM DTT, 200 mM NaCl. The GST-tagged proteins are then eluted by 10 applications (1 ml each) of 25 mM Tris-HCl, pH 7.5, 10 mM reduced-glutathione, 100 mM NaCl, 1 mM DTT, 10% glycerol and stored at −70° C.

Measure of enzyme activity: Tyrosine protein kinase assays with either purified GST-wtRET or GST-RET-Men2B protein are carried out in a final volume of 30 µL containing 15 ng of either GST-wtRET or GST-RET-Men2B protein, 20 mM Tris-HCl, pH 7.5, 1 mM $MnCl_2$, 10 mM $MgCl_2$, 1 mM DTT, 3 µg/ml poly(Glu, Tyr) 4:1, 1% DMSO, 2.0 µM ATP ($\gamma$-[$^{33}$P]-ATP 0.1 µCi). The activity is assayed in the presence or absence of inhibitors, by measuring the incorporation of $^{33}$P from [γ$^{33}$P] ATP into poly(Glu, Tyr) 4:1. The assay is carried out in 96-well plates at ambient temperature for 15 minutes under conditions described above and terminated by the addition of 20 μL of 125 mM EDTA. Subsequently, 40 μL of the reaction mixture are transferred onto Immobilon-PVDF membrane (Millipore) previously soaked for 5 minutes with methanol, rinsed with water, then soaked for 5 minutes with 0.5% H$_3$PO$_4$ and mounted on vacuum manifold with disconnected vacuum source. After spotting all samples, vacuum is connected and each well rinsed with 200 μL 0.5% H$_3$PO$_4$. Membranes are removed and washed 4× on a shaker with 1.0% H$_3$PO$_4$, once with ethanol. Membranes are counted after drying at ambient temperature, mounting in Packard TopCount 96-well frame, and addition of 10 μL/well of Microscint™ (Packard). IC$_{50}$ values are calculated by linear regression analysis of the percentage inhibition of each compound in duplicate, at 4 concentrations (usually 0.01, 0.1, 1 and 10 μM). One unit of protein kinase activity is defined as 1 nmole of $^{33}$P transferred from [γ$^{33}$P] ATP to the substrate protein/minute/mg of protein at 37° C. The compounds of formula I here show IC$_{50}$ values in the range between 0.005 and 20 μM, especially between 0.01 and 1 μM.

VEGF-R1 inhibition can be shown as follows: the test is conducted using Flt-1 VEGF-receptor tyrosine kinase. The detailed procedure is as follows: 30 μl kinase solution (kinase domain of Flt-1, Shibuya et al., Oncogene 5, 519-24 [1990], according to the specific activity, in order to achieve an activity of 4000-6000 counts per minute [cpm] in the sample without inhibitor) in 20 mM Tris.HCl pH 7.5, 3 mM manganese dichloride (MnCl$_2$), 3 mM magnesium chloride (MgCl$_2$) and 3 μg/ml poly(Glu, Tyr) 4:1 (Sigma, Buchs, Switzerland), 8 μM [$^{33}$P]-ATP (0.2 μCi/batch), 1% dimethyl sulfoxide, and 0 to 50 μM of the compound to be tested are incubated together for 10 minutes at room temperature. The reaction is then ended by the addition of 10 μl 0.25 M ethylenediaminetetraacetate (EDTA) pH 7. Using a multichannel dispenser (LAB SYSTEMS, USA), an aliquot of 20 μl is applied to a PVDF (=polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid (H$_3$PO$_4$), incubated for 10 minutes each time while shaking, then mounted in a Hewlett Packard TopCount Manifold and the radioactivity measured after the addition of 10 μl Microscint® (β-scintillation counter liquid; Packard USA). IC$_{50}$-values are determined by linear regression analysis of the percentages for the inhibition of each compound in three concentrations (as a rule 0.01, 0.1, and 1 μM). The IC$_{50}$ values that can be found with the compounds of formula I are in the range of 0.001 to 100 μM, especially in the range from 0.01 to 20 μM.

Analogously to the above test, the efficacy of the compounds according to the invention as inhibitors of VEGF-R2 tyrosine kinase activity can be tested using the VEGF receptor tyrosine kinase KDR. In this test, instead of the Flt-1 kinase domain, the KDR kinase domain (Parast et al., Biochemistry 37 (47), 16788-801 (1998)) is used. The only difference in carrying out this test from the above test lies in the concentration of poly(Glu, Tyr) 4:1 (8 μg/ml), MnCl$_2$ (1 mM) and MgCl$_2$ (10 mM). Compounds of formula I in this instance have IC$_{50}$ values in the range of 0.001 μM to 20 μM, preferred compounds especially in the range of 1 nM to 500 nM.

The inhibition of VEGF-induced receptor autophosphorylation can be confirmed with an in vitro experiments in cells such as transfected CHO cells, which permanently express human VEGF-R2 (KDR), are seeded in complete culture medium (with 10% fetal calf serum=FCS) in 6-well cell-culture plates and incubated at 37° C. under 5% CO$_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20® (polyoxyethylen(20)sorbitane monolaurate, ICI/Uniquema) (PBST). The cell lysates (20 μg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the IC$_{50}$ (inhibitory dose for 50% inhibition). The compounds of formula I here show an IC$_{50}$ in the range of 0.001 to 20 μM, preferred compounds especially between 0.001 and 0.5 μM.

Based on the property of the compounds of formula I as potent VEGF receptor inhibitors, the compounds of formula I are especially suitable for the treatment of diseases associated with deregulated angiogenesis, especially diseases caused by ocular neovascularisation, especially retinopathies such as diabetic retinopathy or age-related macula degeneration, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, including rheumatoid arthritis, fibrotic disorders (e.g. hepatic cirrhosis), diabetes, endometriosis, chronic asthma, arterial or post-transplantational atherosclerosis, neurodegenerative disorders, and especially neoplastic diseases such as cancers (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AML (acute myeloid leukemia), AMM (agnogenic myeloid metaplasia), mesothelioma, glioma and glioblastoma. A compound of formula I is especially suited also to preventing the metastatic spread of tumours and the growth of micrometastases. The compounds of the formula I, due to their activity as kinases, are also useful as in treatment in connection with transplantation.

With the groups of preferred compounds of formula I mentioned hereinafter, definitions of substituents from the general definitions mentioned hereinbefore may reasonably be used, for example, to replace one or more up to all more general definitions with more specific definitions or especially with definitions characterized as being preferred.

Compounds of formula I are prepared analogously to methods that, for other compounds, are in principle known in the art, but are novel when applied in the manufacture of the compounds of the present invention, and are especially prepared according to the methods described hereinbelow under 'Examples' or by analogous methods.

For example, a compound of the formula I can be prepared by reacting
a) for the manufacture of a compound of the formula I wherein Y is O and the other moieties are as defined for a compound of the formula I, a hydroxyl compound of the formula II,

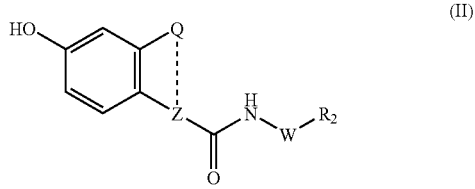

(II)

wherein
Q-Z, W and $R_2$ have the meanings given under formula I, with a halo compound of the formula III,

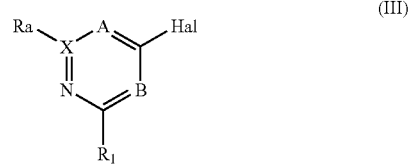

(III)

wherein $R_1$, X, A and B are as defined for a compound of the formula I, Hal is halo, especially chloro or bromo, and Ra is only present if X is not nitrogen (thus forming C-Ra) and is hydrogen or halo, especially chloro or bromo, and if Ra is halo reducing with hydrogen in the presence of a noble metal catalyst to hydrogen;
or
b) a carbonic acid of the formula IV,

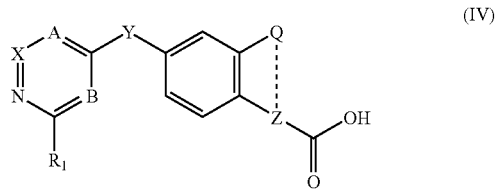

(IV)

or a reactive derivative thereof, wherein
Q-Z, X, A, B, $R_1$ and Y are as defined under formula I, with an amino compound of the formula V,

(V)

wherein W and $R_2$ are as defined for a compound of the formula I;
and, if desired, transforming a compound of formula I into a different compound of formula I, transforming a salt of an obtainable compound of formula I into the free compound or a different salt, transforming an obtainable free compound of formula I into a salt thereof, and/or separating an obtainable mixture of isomers of a compound of formula I into individual isomers.

The reaction under a) preferably takes place in the presence of an appropriate solvent and a base, e.g. in N-methylpyrrolidine in the presence of an alkaline metal phosphate, such as potassium phosphate, for example at temperatures from 0° C. to the reflux temperature of the corresponding reaction mixture.

The reduction of halo Ra into hydrogen, if Ra is hydrogen, then subsequently takes place e.g. by hydrogenation in the presence of a noble metal catalyst, such as palladium or platinum, preferably on a carrier, such as coal, in an appropriate solvent, such as water, tetrahydrofurane or mixtures thereof, and a tertiary nitrogen base, such as tri-lower alkylamine, e.g. triethylamine, for example at temperatures from 0° C. to the reflux temperature of the corresponding reaction mixture.

The amide bond formation under b) preferably takes place, if the reactive derivative of the carbonic acid of the formula IV is a lower alkyl ester (with CO—O-lower alkyl instead of the carboxy group), e.g. by Lewis acid mediated N-acylation by first adding a Lewis acid, especially a tri-lower alkylaluminium, such as trimethylaluminium, to the amine of the formula V, e.g. in an appropriate solvent such as toluene, e.g. at temperatures from 0 to 30° C., and then adding the lower alkyl ester of the formula IV, if desired, in another solvent, such as tetrahydrofurane, and heating, e.g. to a temperature from 30 to 120° C.; or, if the reactive derivative is a carbonic acid halogenide (with a group CO-Hal, wherein Hal is halo, preferably chloro or bromo, instead of the carboxy group in formula IV; obtainable e.g. by reacting the free carbonic acid of the formula IV with oxalyl chloride in an appropriate solvent, such as methylene chloride, e.g. at temperatures in the range from 0 to 50° C.) in an appropriate solvent, such as methylene chloride, e.g. at temperatures from 0 to 50° C.; or by forming the reactive derivative of the carbonic acid of the formula IV in situ using customary condensation reagents, such as HBTU, HAT or the like.

A compound of the formula IA (or a corresponding starting material) may be converted into a different compounds of the formula I.

For example, a compound of the formula I (or a corresponding precursor e.g. of the formula III or IV) wherein $R_1$ is halo (especially chloro) can be converted
(i) into the corresponding compound wherein $R_1$ is lower alkylamino by reaction with a lower alkylamine, e.g. in the presence of an appropriate solvent, such as tetrahydrofurane, e.g. at elevated temperatures, for example from 30 to 80° C.;
(ii) into the corresponding compound wherein $R_1$ is amino by reaction first with an alkaline metal azide, e.g. sodium azide, in an appropriate solvent, such as dimethylformamide, e.g. at elevated temperatures, for example from 30 to 75° C., followed by reduction, m e.g. by hydrogenation in the presence of a noble metal catalyst, such as palladium on charcoal, in an appropriate solvent, e.g. at temperatures in the range from 0 to 50° C., to the amino group;
(iii) into the corresponding compound wherein $R_1$ is lower alkoxycarbonylamino by reaction of the corresponding compound with an amino group obtainable as described under (ii) in the presence of a lower alkyl-chloroformate or the like in an appropriate solvent, e.g. methylene chloride, in the presence of a tertiary nitrogen base, e.g. pyridine, at temperatures e.g. from 0° C. to the reflux temperature of the reaction mixture;
(iv) into the corresponding compound wherein $R_1$ is lower alkylsulfonylamino (lower alkyl-S(=O)$_2$—) by reaction of the amino group obtainable as described under (ii) in the presence of a corresponding reactive lower alkylsulfonic acid derivative, e.g. an anhydride, in the presence of an appropriate solvent, e.g. methylene chloride, and a tertiary nitrogen base, e.g. pyridine, e.g. at temperatures in the range from 0 to 50° C.;
(v) into the corresponding compound wherein $R_1$ is N-lower alkylaminocarbonylamino, by reaction of the amino group obtainable as described under (ii) with a corresponding lower alkyl isocyanate in the presence of an appropriate solvent, e.g. tetrahydrofurane, preferably at elevated temperatures, e.g. from 50° C. to the reflux temperature of the reaction mixture, e.g. at 100° C.;
(vi) into the corresponding compound wherein $R_1$ is lower alkanoylamino by reaction with the corresponding lower alkanolamide in the presence of cesium carbonate, catalysts such as tris(dibenzylideneacetone)dipalladium and (9,9-dimethyl-9H-xanthene-4,5-diyl)bis[diphenyl-phosphine] and an appropriate solvent, such as dioxane, e.g. at temperatures in the range from 0 to 80° C.

A compound of the formula I wherein $R_1$ is hydroxyl can be converted into the corresponding compound wherein $R_1$ is halo, e.g. chloro, e.g. by reaction with an inorganic acid halide, e.g. PO(Hal)$_3$ wherein Hal is halo, especially chloro, in an appropriate solvent, such as acetonitrile, in the presence of a corresponding tetra-(lower alkyl)ammonium halogenide and a tertiary nitrogen base, e.g. N,N-dimethylaniline, at elevated temperatures, e.g. from 30 to 80° C. The corresponding halo compound can then be further converted as described in the preceding paragraph.

The starting materials used in the preparation of the compounds of formula I are known, capable of being prepared according to known processes, or commercially obtainable. In particular, the anilines to be used as starting material in the preparation of the compounds of formula I can be prepared as described in WO 03/099771, WO 05/051366 or in the examples of the present invention or by analogy thereto, are commercially available or can be prepared according to known processes. Starting materials and appropriate manufacturing methods can also be deduced from copending patent application PCT/IB2005/004030, that was published under the International Publication Number WO2006/059234 which is here, especially regarding such materials and manufacturing methods, incorporated by reference, as well as from the reference examples.

For example,
a starting material of the formula II wherein W and $R_2$ are as described in formula I and Q-Z is O—CH$_2$—N can for example be prepared as described in or in analogy to Example 1, Step 1.2 and the preceding steps;
a starting material of the formula IV wherein $R_1$ is hydroxyl, A is N, B and X are each CH, Y is CH$_2$ and Q-Z is CH=CH—CH=C can be prepared by or in analogy to the method described in Example 3 Step 3.8 and preceding steps or as described in Example 9, Step 9.2 and preceding steps;
a starting material of the formula IV wherein $R_1$ is as defined under formula I, A is N, B and X are CH and Y is O can, for example, be prepared as described in or in analogy to Example 10 Step 10.2 and preceding steps;
a starting material of the formula IV wherein $R_1$ is lower alkoxyalkyl and the other moieties are as described under formula IV can for example be prepared as described in Example 15 Step 15.4 and preceding steps; and so on.

Compounds of the formula III and/or V can be prepared by methods as described in the examples or in analogy thereto.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula IA is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/1, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, proteolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H⁺ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula IA described as being preferred. The invention also relates to novel intermediates and/or starting materials. Special preference is given to reaction conditions and novel intermediates that are identical or analogous to those mentioned in the Examples.

Pharmaceutical Methods, Preparations and the Like

The invention relates also to pharmaceutical compositions comprising a compound of formula I, to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The pharmacologically acceptable compounds of the present invention may be present in or employed, for example, for the preparation of pharmaceutical compositions that comprise an effective amount of a compound of the formula I, or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment of (this, in a broader aspect of the invention, also includes the prevention of (=prophylaxis against)) a disease that responds to inhibition of protein kinase activity, comprising an amount of a compound of formula I or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase and/or a proliferative disease, which comprises administering a (against the mentioned diseases) prophylactically or especially therapeutically effective amount of a compound of formula I according to the invention, or a tautomer thereof or a pharmaceutically acceptable salt thereof, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

A compound of the formula I may also be used to advantage in combination with other anti-proliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further antiangiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, rogletimide, pyridoglutethimide, trilostane, testrolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, colchicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, e.g.:
a) compounds targeting, decreasing or inhibiting the activity of the fibroblast growth factor-receptors (FGF-Rs);
b) compounds targeting, decreasing or inhibiting the activity of the insulin-like growth factor I receptor (IGF-IR), especially compounds which inhibit the IGF-IR, such as those compounds disclosed in WO 02/092599;
c) compounds targeting, decreasing or inhibiting the activity of the Trk receptor tyrosine kinase family;
d) compounds targeting, decreasing or inhibiting the activity of the Axl receptor tyrosine kinase family;
e) compounds targeting, decreasing or inhibiting the activity of the c-Met receptor;
f) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor);
g) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzene-malonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxy-phenyl)methyl]amino}-benzoic acid adamantyl ester; NSC 680410, adaphostin); and
h) compounds targeting, decreasing or inhibiting the activity of the epidermal growth factor family of receptor tyrosine kinases (EGF-R, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HERCEPTIN), cetuximab, Iressa, erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α- γ- or δ-tocopherolor α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. benzamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or any combination thereof.

Preferred compounds of the formula I (which are also preferred for pharmaceutical compositions, methods and uses according to the invention), tautomers and/or salts thereof can be deduced from the dependent claims which are incorporated here by reference.

Among the preferred compounds of the formula I are those wherein
$R_1$ is hydroxyl, lower alkoxy-lower alkyl, amino-lower alkylamino, or N-mono- or N,N-di-(lower alkyl)amino-lower alkylamino, and
$R_2$ is phenyl substituted by one or two moieties independently selected from lower alkyl, $C_3$-$C_8$-cycloalkyl, halo, halo-lower alkyl, halo-lower alkoxy or by lower alkoxy, or is 2H-pyrazolyl substituted by halophenyl and lower alkyl;
while the other symbols are as defined for formula I in claim 1.

Preferred is also a compound of the formula I wherein
$R_1$ is halo, piperazinyl-lower alkylamino or N-lower alkylpiperazinyl-lower alkylamino, and
$R_2$ can also be 2H-pyrazolyl substituted by halophenyl and lower alkyl;
while the other symbols are as defined for formula I in claim 1.

The invention relates especially to compounds of the formula I as given in the examples (especially in example 10, 12 or 14), tautomers thereof and/or pharmaceutically acceptable salts thereof.

The following Examples serve to illustrate the invention without limiting the scope thereof.

EXAMPLES

Temperatures are measured in degrees Celsius. Unless otherwise indicated, the reactions take place at room temperature under $N_2$-atmosphere.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

Abbreviations:

| | Abbreviations: |
|---|---|
| Anal. | elemental analysis (for indicated atoms, difference between calculated and measured value ≦0.4%) |
| aq. | aqueous |
| brine | saturated solution of NaCl in water |
| celite | Celite ® (filtering aid based on diatomaceous earth; Celite Corporation, Lompoc, USA) |
| conc. | concentrated |
| DIPE | diisopropyl-ether |
| DMAP | dimethylaminopyridine |
| DMEU | 1,3-dimethyl-2-imidazolidinone |
| DMF | dimethyl formamide |
| DMSO | dimethyl sulfoxide |
| ether | diethylether |

31
-continued

Abbreviations:

| | |
|---|---|
| Et₃N | triethylamine |
| EtOAc | ethyl acetate |
| EtOH | ethanol |
| eq. | equivalent |
| Ex. | Example |
| h | hour(s) |
| HPLC | high pressure liquid chromatography |
| Hyflo | Hyflo Super Cel ® (filtering aid based on diatomaceous earth; obtainable from Fluka, Buchs, Switzerland) |
| HOAc | acetic acid |
| HV | high vacuum |
| l | litre(s) |
| Me | methyl |
| MeOH | methanol |
| min | minute(s) |
| m.p. | melting point |
| MPLC | medium pressure liquid chromatography Combi Flash Companion system from Isco, Inc.; Columns: RediSep ® flash column, Teledyne Isco, filled with 4 g, 12 g, 40 g or 120 g of SiO₂; application to column: either mixture is dissolved as a concentrated solution in eluent, or a solution of the mixture is concentrated together with SiO₂ in vacuo and applied as powder) Gilson system: reversed phase Nucleosil C18 (H₂O/CH₃CN + TFA), generally product obtained as free base after neutralization with NaHCO₃ |
| MS | mass spectrum |
| NMP | N-methyl-pyrrolidone |
| Ph | phenyl |
| | propylphosphonic anhydride: 2,4,6-tripropyl-1,3,5,2,4,6-trioxatriphophorinane-2,4,6-trioxide [68957-94-8]; 50% in DMF |
| $R_f$ | ratio of fronts (TLC) |
| rt | room temperature |
| sat. | saturated |
| THF | tetrahydrofuran (distilled from Na/benzophenone) |
| TFA | trifluoroacetic acid |
| TLC | thin layer chromatography |
| $t_{Ret}$ | retention time (HPLC) |

HPLC Conditions:

$t_{Ret}$: retention time [min] for System A: Linear gradient 20-100% CH₃CN (0.1% TFA) and H₂O (0.1% TFA) in 13 min+5 min 100% CH₃CN (0.1% TFA); detection at 215 nm, flow rate 1 ml/min at 25 or 30° C. Column: Nucleosil 120-3 C18 (125×3.0 mm).

Anilines used as educts: Most respective anilines are either commercially available or described in WO 03/099771, WO 05/051366 or EP 1375482 or can be prepared analogously to the derivatives exemplified therein.

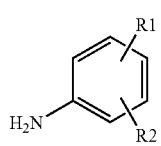

Example 1

6-(2-Chloro-pyrimidin-4-yloxy)-benzooxazole-3-carboxylic acid (4-chloro-3-trifluoromethyl-phenyl)-amide

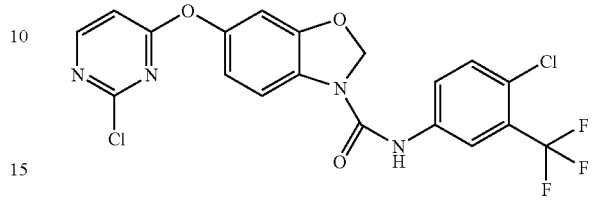

To a solution of 290 mg (0.81 mMol) 6-hydroxy-benzooxazole-3-carboxylic acid (4-chloro-3-trifluoromethyl-phenyl)-amide (Step 1.3) and 134 mg (0.90 mMol) 2,4-dichloro-pyrimidine in 15 ml NMP, 377 mg (1.78 mMol) K₃PO₄ are added. After 2 h at rt the reaction mixture is dissolved in EtOAc and water, the aq. phase separated off and extracted twice with EtOAc. The organic layers are washed with water and brine, dried (Na₂SO₄) and concentrated. Chromatography (Combi Flash; CH₂Cl₂→CH₂Cl₂/EtOAc 9:1) gives the title compound: m.p.: 140-142° C.; MS: [M+1]⁺=471/473.

The starting material is prepared as follows:

Step 1.1: 1-(4-Benzyloxy-2-hydroxy-phenyl)-3-(4-chloro-3-trifluoromethyl-phenyl)-urea To a solution of 1.00 g (4.6 mMol) 2-amino-5-benzyloxy-phenol [preparation see: WO 03/045925; page 146] in 15 ml THF, a solution of 1.1 g (5.0 mMol) 4-chloro-3-trifluoromethyl-phenylisocyanate in 15 ml THF is added dropwise. After 75 min at rt, the reaction mixture is diluted in water and EtOAc, the aq. phase separated off and extracted twice with EtOAc. The organic layers are washed with water and brine, dried (Na₂SO₄) and concentrated. Trituration from hexane gives the crystalline title compound: m.p.: 182-184° C.; HPLC: $t_{Ret}$=17.5.

Step 1.2: 6-Benzyloxy-benzooxazole-3-carboxylic acid (4-chloro-3-trifluoromethyl-phenyl)-amide To a solution of 1.4 g (3.2 mMol) of 1-(4-benzyloxy-2-hydroxy-phenyl)-3-(4-chloro-3-trifluoromethyl-phenyl)-urea in 420 ml DMEU, 700 mg NaH (55% in oil; 16 mMol) are given. After 15 min, 23 ml of CH₂Br₂ are added and stirring is continued for 6 h. Then 1 ml of formic acid is added and the resulting mixture is evaporated in HV. The residue is dissolved in EtOAc and water. The separated aq. phase is extracted twice with EtOAc. The organic layers are washed with water and brine, dried (Na₂SO₄) and concentrated. Chromatography (Combi Flash; hexane/CH₂Cl₂ 1:1→CH₂Cl₂) gives the title compound: m.p.: 135-136° C.

Step 1.3: 6-Hydroxy-benzooxazole-3-carboxylic acid (4-chloro-3-trifluoromethyl-phenyl)-amide As a solution in 25 ml THF, 469 mg (1.04 mMol) 6-benzyloxy-benzooxazole-3-carboxylic acid (4-chloro-3-trifluoromethyl-phenyl)-amide are hydrogenated during 1 h in the presence of 267 mg Pd/C (10%). The catalyst is filtered off, washed with THF and the filtrate concentrated. Trituration

Example 2

6-(2-Methylamino-pyrimidin-4-yloxy)-benzooxazole-3-carboxylic acid (4-chloro-3-trifluoromethyl-phenyl)-amide

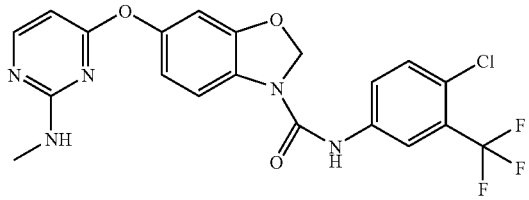

A solution of 50 mg (0.106 mMol) 6-(2-chloropyrimidin-4-yloxy)-benzooxazole-3-carboxylic acid (4-chloro-3-trifluoromethyl-phenyl)-amide in 1.5 ml THF and 107 μl MeNH$_2$ (2 M in THF; 0.214 mMol) is stirred in a sealed vessel for 24 h at rt. Concentration of the reaction mixture and chromatography (Combi Flash; hexane/EtOAc 4:1-1:1) gives the title compound: MS: [M+1]$^+$=466; HPLC: $t_{Ret}$=13.8; TLC(hexane/EtOAc 1:1): $R_f$=0.09.

Example 3

6-(6-Hydroxy-pyrimidin-4-ylmethyl)-naphthalene-1-carboxylic acid (4-fluoro-3-trifluoromethyl-phenyl)-amide

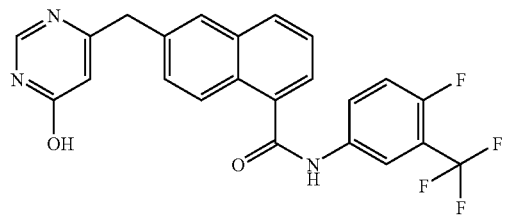

345 mg (1.23 mMol) 6-(6-hydroxy-pyrimidin-4-ylmethyl)-naphthalene-1-carboxylic acid (Step 3.8), 193 μl (1.5 mMol) 4-fluoro-3-trifluoromethyl-aniline, 1.7 ml (12.3 mMol) Et$_3$N and 63 mg (0.52 mMol) DMAP are dissolved in 10 ml of dry DMF. Then a solution of 1.45 ml (50% in DMF; 2.48 mMol) propylphosphonic anhydride is added. After 20 min, the reaction mixture is poured into water, brine and EtOAc. The separated aq. phase is extracted twice with EtOAc. The organic layers are washed with water and brine, dried (Na$_2$SO$_4$) and concentrated. Chromatography (Combi Flash; CH$_2$Cl$_2$→CH$_2$Cl$_2$/MeOH 1:19) gives the title compound: MS: [M+1]$^+$=442; TLC (CH$_2$Cl$_2$/MeOH 1:9): $R_f$=0.37; $^1$H-NMR (DMSO-d$_6$): δ ppm 12.43 (s, 1H), 10.92 (s, HN), 8.36 (m, 1H), 8.17 (d, 1H), 8.11 (m, 3H), 7.92 (s, 1H), 7.78 (d, 1H), 7.7-7.5 (m, 3H), 6.25 (s, 1H), 3.99 (s, H$_2$C).

The starting material is prepared as follows:

Step 3.1: 6-Trifluoromethanesulfonyloxy-naphthalene-1-carboxylic acid methyl ester A solution of 17.6 g (87 mMol) 6-hydroxy-naphthalene-1-carboxylic acid methyl ester (obtained by reaction of the free carbonic acid precursor with trimethylsilylchloride in methanol), 24.3 ml (174 mMol) Et$_3$N and 0.53 g (4.3 mMol) DMAP in 300 ml of THF is cooled in an ice-bath. Then 34.2 g (95.7 mMol) N-phenyl-bis(trifluoromethanesulfonimide) (Fluka; Buchs/Switzerland), dissolved in 200 ml THF are added dropwise during 20 min. After 15 min, the mixture is warmed up to rt and stirring is continued at rt for 80 min. The mixture is partially concentrated in vacuo and the residue re-dissolved in sat. NaHCO$_3$ solution and EtOAc. The aq. phase is separated off and discarded. The organic layer is washed twice with water, water/sat. NaHCO$_3$ solution 1:3 and brine, dried (Na$_2$SO$_4$) and concentrated. This crude product is used in the next step without further purification: HPLC: $t_{Ret}$=17.4.

Step 3.2: 6-Trimethylsilanylethynyl-naphthalene-1-carboxylic acid methyl ester A solution of 15.6 ml (113 mMol) ethynyl-trimethylsilane (Fluka; Buchs/Switzerland) and 15.7 ml (113 mMol) Et$_3$N in 250 ml degassed DMF is added to 34 g (102 mMol) 6-trifluoromethanesulfonyloxy-naphthalene-1-carboxylic acid methyl ester, 1.0 g (5.2 mMol) CuI and 5.0 g (7.1 mMol) Pd(PPh$_3$)$_2$Cl$_2$ in 250 ml of degassed DMF. After 15 h at rt, the mixture is concentrated partially in vacuo at 40° C. and the residue re-dissolved in sat. NaHCO$_3$ solution and EtOAc. The aq. phase is separated off and extracted twice with EtOAc. The organic layer is washed twice with sat. NaHCO$_3$ solution, water/sat. NaHCO$_3$ solution 1:1 and brine, dried (Na$_2$SO$_4$) and concentrated. Column chromatography (SiO$_2$; hexane/EtOAc 199:1) gives the title compound as an oil: MS: [M+1]$^+$= 283; TLC(hexane/EtOAc 19:1): $R_f$=0.22.

Step 3.3: 6-Carboxymethyl-naphthalene-1-carboxylic acid methyl ester 21 ml (0.22 Mol) borane dimethylsulfide complex are added dropwise during 15 min to an ice-cooled solution of 50.2 ml (495 mMol) cyclohexene in 400 ml of THF. The mixture is stirred for 2.5 h at rt and again cooled in an ice-bath. Then a solution of 23.29 g (82.5 mMol) trimethylsilanylethynyl-naphthalene-1-carboxylic acid methyl ester in 400 ml of THF is added dropwise. The mixture is warmed up to rt and stirred for 1 h. Then 585 ml sat. NaHCO$_3$ solution and 138 ml H$_2$O$_2$ (30% in H$_2$O) are added slowly (cool to keep temperature below 60° C.). The suspension is stirred for 16 h and then concentrated in vacuo. The residue is diluted with 1 l sat. NaHCO$_3$ solution, 375 ml water and EtOAc, the organic layer is separated off and washed with 0.5 l sat. NaHCO$_3$ solution and 250 ml water and discarded. The aq. phases are acidified by addition of 4 N HCl (pH=2) and extracted with 3 portions of EtOAc. The organic layers are dried (MgSO$_4$) and concentrated. Trituration from hexane affords the title compound: MS: [M+1]$^+$=245; HPLC: $t_{Ret}$=12.3.

Step 3.4: 6-Chlorocarbonylmethyl-naphthalene-1-carboxylic acid methyl ester 140 μl (1.8 mMol) DMF are added to an ice-cooled solution of 3.6 ml (43 mMol) oxalylchloride in 150 CH$_2$Cl$_2$. Then a suspension of 8.8 g (36 mMol) 6-carboxymethyl-naphthalene-1-carboxylic acid methyl ester in 400 ml CH$_2$Cl$_2$ is added during 1 h. After 1.5 h stirring in the ice-bath, the reaction mixture is concentrated in vacuo, yielding the title compound.

Step 3.5: 6-(3-Ethoxycarbonyl-2-oxo-propyl)-naphthalene-1-carboxylic acid methyl ester A solution of 8.56 g (64.8 mMol) of malonic acid monoethyl ester and 112 mg (0.72 mMol) 2,2'-bipyridine in 200 ml THF is cooled to −78° C. Then 60 ml of a 1.6 M solution of ″butyllithium in THF are added dropwise (color changes from yellow to red!). Warming the mixture up to −10° C., renders the mixture turn to yellow again. Addition of another 10 ml of a 1.6 M solution of ″butyllithium in THF results in a persistent red color of the mixture. After cooling to −78° C., a suspension of 36 mMol 6-chlorocarbonylmethyl-naphthalene-1-carboxylic acid methyl ester in 250 ml THF is added during 40 min and then stirring is continued for 1 h. The dark mixture is poured into 200 ml of 1 N HCl and 400 ml ether, the aq. phase separated off and extracted with 2 portions of EtOAc. The organic layers are washed with brine, dried ($Na_2SO_4$) and concentrated to the title compound which can be used in the Step 3.6 as such. Pure product can be obtained by chromatography (Combi Flash; hexane/EtOAc 85:15): MS: [M−1]=313; HPLC: $t_{Ret}$=15.5.

Step 3.6: 6-(6-Oxo-2-thioxo-1,2,3,6-tetrahydro-pyrimidin-4-ylmethyl)-naphthalene-1-carboxylic acid 3.46 g (45.4 mMol) thiourea are added to a solution of 29.7 mMol 6-(3-ethoxycarbonyl-2-oxo-propyl)-naphthalene-1-carboxylic acid methyl ester in 25 ml tert-butanol. Then 13.3 g (119 mMol) potassium tert-butyrate are added (exothermic). After 50 min, the mixture is heated for 4.5 h in an oil bath of 100° C. Cooling to rt gives an almost solid mixture, which is redissolved by addition of 59 ml of a 1 M aq. solution of LiOH and stirring during 40 min. This solution is diluted with 500 ml of a 0.33 M solution of NaOH and EtOAc. The organic phase is separated off, washed with 300 ml of a 0.33 M solution of NaOH and discarded. The aq. phases are acidified by addition of 2 N HCl (pH=3), the precipitated product filtered off, washed with 0.001 N HCl and dried in vacuo at 80° C. The crude material is stirred in a boiling mixture of 0.6 l $CH_3CN$, 60 ml EtOAc, 120 ml MeOH and 120 ml THF. Filtration of the hot suspension then leads to the title compound: m.p.: 334-337° C.

Step 3.7: 6-(6-Hydroxy-2-methylsulfanyl-pyrimidin-4-ylmethyl)-naphthalene-1-carboxylic acid 2.30 g (7.37 mMol) 6-(6-oxo-2-thioxo-1,2,3,6-tetrahydro-pyrimidin-4-ylmethyl)-naphthalene-1-carboxylic acid are suspended in 160 ml THF. Then a solution of 452 mg (11.3 mMol) NaOH in 9 ml water is added, followed by 556 μl (8.93 mMol) methyliodide. After 15 h, the reaction mixture is concentrated in vacuo. The residue is used without further purification in Step 3.8. Pure title compound can be obtained by chromatography (Combi Flash; $CH_2Cl_2$→$CH_2Cl_2$/MeOH 7:1): TLC ($CH_2Cl_2$/MeOH 4:1): $R_f$=0.46.

Step 3.8: 6-(6-Hydroxy-Pyrimidin-4-ylmethyl)-naphthalene-1-carboxylic acid 29 g Raney Nickel in EtOH are added to a solution of 5.08 mMol 6-(6-hydroxy-2-methylsulfanyl-pyrimidin-4-ylmethyl)-naphthalene-1-carboxylic acid in 220 ml EtOH and 170 ml water. The mixture is stirred for 3.5 h at 80° C., filtered hot and the residue is extensively washed with EtOH/$H_2O$ 1:1. Partial concentration in vacuo, acidification of the residue with 1 N HCl (pH=1), filtration of the precipitated product, washing with 50 ml 0.1 N HCl and drying (HV; 90° C.) gives the title compound. Additional product can be isolated from the filtrate by extraction with 3 Portions of EtOAc, washing of the organic layers with brine, drying ($Na_2SO_4$), concentration and chromatography (Combi Flash; $CH_2Cl_2$→$CH_2Cl_2$/MeOH+0.5% HOAc 19:1): TLC ($CH_2Cl_2$/MeOH+0.5% HOAc 9:1): $R_f$=0.17.

Example 4

6-(6-Hydroxy-pyrimidin-4-ylmethyl)-naphthalene-1-carboxylic acid (3-trifluoromethyl-phenyl)-amide

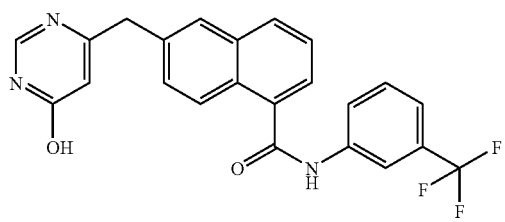

Prepared from 6-(6-hydroxy-pyrimidin-4-ylmethyl)-naphthalene-1-carboxylic acid (Step 3.8) and 3-trifluoromethyl-aniline analogously to Ex. 3: MS: [M+1]$^+$=424; TLC ($CH_2Cl_2$/MeOH 9:1): $R_f$=0.26.

Example 5

6-(6-Chloro-Pyrimidin-4-ylmethyl)-naphthalene-1-carboxylic acid (4-fluoro-3-trifluoromethyl-phenyl)-amide

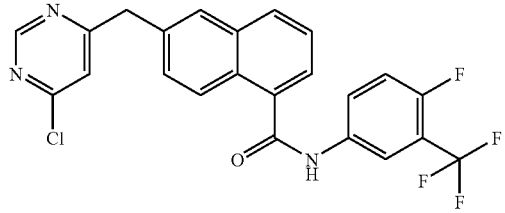

To a solution of 200 mg (0.453 mMol) 6-(6-hydroxy-pyrimidin-4-ylmethyl)-naphthalene-1-carboxylic acid (4-fluoro-3-trifluoromethyl-phenyl)-amide in 15 ml $CH_3CN$, 165.7 mg (1.0 mMol) tetrmethylammonium chloride, 127 μl (1.0 mMol) N,N-dimethylaniline and 0.55 ml (6.0 mMol) $POCl_3$ are added. The mixture is heated up to 75° C. for 1 h, cooled to rt and poured into 30 g ice. After 1 h of vigorous stirring, the title compound can be filtered off and washed with 6 ml $CH_3CN$/$H_2O$ 1:2: MS: [M+1]$^+$=460/462; HPLC: $t_{Ret}$=16.5.

Example 6

6-(6-Methylamino-pyrimidin-4-ylmethyl)-naphthalene-1-carboxylic acid (4-fluoro-3-trifluoromethyl-phenyl)-amide

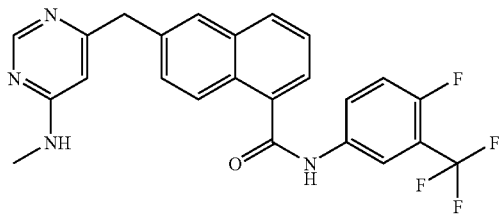

A solution of 40 mg (0.087 mMol) 6-(6-chloro-pyrimidin-4-ylmethyl)-naphthalene-1-carboxylic acid (4-fluoro-3-trifluoromethyl-phenyl)-amide and 750 µl methylamine (2 M in THF; 1.5 mMol) in 1.5 ml THF is stirred in a sealed vessel for 20 h at rt and 3.5 h at 65° C. Concentration and chromatography (Combi Flash; EtOAc→EtOAc/EtOH 9:1) gives the title compound: MS: [M+1]⁺=455; TLC(EtOAc/EtOH 9:1): $R_f$=0.27.

Example 7

6-(6-Amino-pyrimidin-4-ylmethyl)-naphthalene-1-carboxylic acid (4-fluoro-3-trifluoromethyl-phenyl)-amide

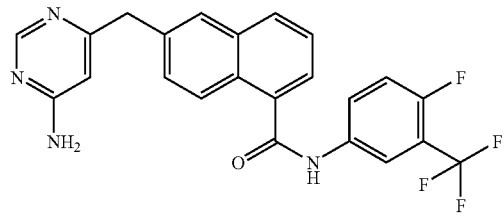

A mixture of 200 mg (0.435 mMol) 6-(6-chloro-pyrimidin-4-ylmethyl)-naphthalene-1-carboxylic acid (4-fluoro-3-trifluoromethyl-phenyl)-amide and 50 mg (0.76 mMol) NaN₃ in 5 ml DMF is stirred for 2 h at 60° C., giving 6-(6-azido-pyrimidin-4-ylmethyl)-naphthalene-1-carboxylic acid (4-fluoro-3-trifluoromethyl-phenyl)-amide (MS: [M+1]⁺=467). After cooling to rt, 50 mg Pd/C (10%; Engelhard 4505) are added and the mixture is hydrogenated under a H₂-atmosphere for 30 min. Filtration through Celite, concentration and chromatography (Combi Flash; CH₂Cl₂/MeOH 9:1→1:1) gives the title compound: MS: [M+1]⁺=441; HPLC: $t_{Ret}$=12.3.

Example 8

{6-[5-(4-Fluoro-3-trifluoromethyl-phenylcarbamoyl)-naphthalen-2-ylmethyl]-pyrimidin-4-yl}carbamic acid methyl ester

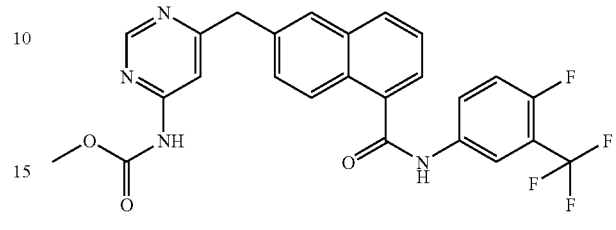

0.4 ml (5 mMol) methyl chloroformate are added to a solution of 54 mg (0.123 mMol) 6-(6-amino-pyrimidin-4-ylmethyl)-naphthalene-1-carboxylic acid (4-fluoro-3-trifluoromethyl-phenyl)-amide in 1 ml CH₂Cl₂ and 1.5 ml pyridine. After 20 h, the solution is diluted with EtOAc and water, the aq. phase separated off and extracted twice with EtOAc. The organic layers are washed with water and brine, dried (Na₂SO₄) and concentrated. Chromatography (Combi Flash; CH₂Cl₂→CH₂Cl₂/MeOH 92:8) gives the title compound: MS: [M+1]⁺=499; TLC (CH₂Cl₂/MeOH 85:15): $R_f$=0.54; ¹H-NMR (DMSO-d₆): δ ppm 10.86 (s, HN), 10.65 (s, HN), 8.69 (s, 1H), 8.30 (d, 1H), 8.13 (d, 1H), 8.03 (m, 2H), 7.90 (s, 1H), 7.74 (m, 2H), 7.58 (t, 1H), 7.50 (m, 2H), 4.22 (s, H₂C), 3.64 (s, H₃C).

Example 9

6-(6-Acetylamino-pyrimidin-4-ylmethyl)-naphthalene-1-carboxylic acid [4-(4-methyl-piperazin-1-ylmethyl)-3-trifluoromethyl-phenyl]-amide

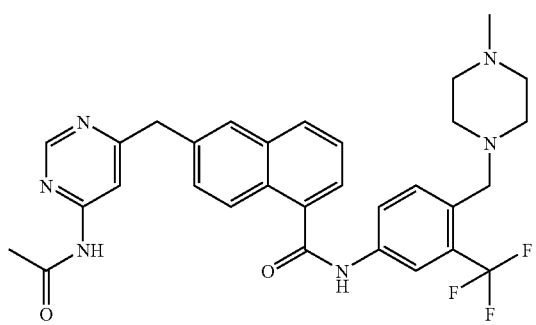

A solution of 2 ml trimethylaluminium (2 M in toluene, 4 mMol) is added to a stirred solution of 355 mg (1.3 mMol) 4-(4-methyl-piperazin-1-ylmethyl)-3-trifluoromethyl-phenylamine in 20 ml toluene at 10° C. under an argon atmosphere. After 1 h at r t, a solution of 436 mg (1.3 mMol) 6-(6-acetylaminopyrimidin-4-ylmethyl)-naphthalene-1-carboxylic acid methyl ester (Step 9.2) in 5 ml THF is added and the reaction mixture is heated at 90° C. for 45 min. After cooling to 5° C., a solution of sat. aqueous ammonium chloride (50 ml) is added dropwise. The mixture is poured into EtOAc and filtered over hyflo. The separated aq. phase is extracted with EtOAc. The combined organic phases are washed with water and brine, dried (Na₂SO₄) and concentrated. The crude product is purified by chromatography (SiO$_2$, CH$_2$Cl$_2$/EtOH/NH$_3$ 90:9:1) and is recrystallised from hot EtOAc and hexane to afford the title compound as a colourless solid: m.p.: 202-204° C.

The starting material is prepared as follows:

Step 9.1:
N-(6-Trimethylstannanyl-pyrimidin-4-yl)-acetamide

A solution of 0.46 ml (2.2 mMol) hexamethyldistannane in toluene is added dropwise to a stirred mixture of 343 mg (2 mMol) N-(6-chloro-pyrimidin-4-yl)-acetamide (obtainable from 4,6-dichloropyrimidine by reaction with NH$_3$ in water and isopropanol at 55° C. and acetylation of the resulting 4-amino-6-chloro-pyrimidine with acetanhydride in the presence of LiCl at 110° C.) and 92 mg (0.08 mMol) tetrakis (triphenylphosphine)palladium in 20 ml toluene under an argon atmosphere. The reaction mixture is then heated at 120° C. for 6 h. After cooling to rt, the solvent is evaporated off under reduced pressure to give the title compound as a brown residue which is used in the next Step without further purification.

Step 9.2: 6-(6-Acetylamino-pyrimidin-4-ylmethyl)-naphthalene-1-carboxylic acid methyl ester A mixture of 560 mg (2 mMol) 6-bromomethyl-naphtalene-1-carboxylic acid methyl ester (synthesized according to W. L. Cody et al.: *Bioorg. Med. Chem.* 2005, 13, 59), 92 mg (0.08 mMol) tetrakis(triphenylphosphine)palladium and N-(6-trimethylstannanol-pyrimidin-4-yl)-acetamide in 20-ml toluene is heated under an argon atmosphere at 120° C. for 14 h. The cooled suspension is diluted with EtOAc and water, stirred whilst bubbling air through the mixture for 30 min and filtered (hyflo). The organic phase is separated and washed with a sat. solution of brine. The aq. phase is extracted twice with EtOAc and the combined organic extracts are dried over Na$_2$SO$_4$. The solvent is evaporated off under reduced pressure and the residue is purified by chromatography (SiO$_2$, EtOAc) and recristallized from EtOAc/Hexane to afford the title compound as a beige solid: m.p.: 158-160° C.

Example 10

{4-[5-(4-Fluoro-3-trifluoromethyl-phenylcarbamoyl)-naphthalen-2-yloxy]-pyrimidin-2-yl}carbamic acid methyl ester

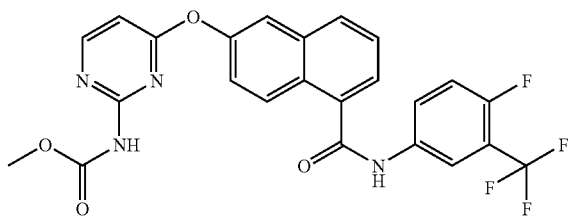

126 μl (1.64 mMol) methyl chloroformate are added portionwise to a solution of 300 mg (0.68 mMol) 6-(2-amino-pyrimidin-4-yloxy)-naphthalene-1-carboxylic acid (4-fluoro-3-trifluoromethyl-phenyl)-amide (Step 10.3) in 7 ml CH$_2$Cl$_2$ and 7 ml pyridine during 2 h. After 4 h, the solution is diluted with EtOAc and water, the aq. phase separated off and extracted twice with EtOAc. The organic layers are washed with water and brine, dried (Na$_2$SO$_4$) and concentrated. Precipitation with DIPE and filtration gives the title compound: m.p.: 204-205° C.

The starting material is prepared as follows:

Step 10.1: 6-(2-Amino-6-chloro-pyrimidin-4-yloxy)-naphthalene-1-carboxylic acid

A suspension of 6.56 g (40 mMol) 2-amino-4,6-dichloropyrimidine and 7.52 g (40 mMol) 6-hydroxy-1-naphthoic acid in 160 ml acetone and 80 ml 1 N aqueous NaOH is heated to 62° C. for 36 h. The mixture is cooled to rt, partially concentrated in vacuo and the residue poured into 1.6 l icewater. Under vigorous stirring, 20 ml 2 N HCl are added dropwise (pH≈4). After stirring the suspension for 30 min, the title compound is filtered off and washed with water; HPLC: t$_{Ret}$=12.8.

Step 10.2: 6-(2-Amino-pyrimidin-4-yloxy)-naphthalene-1-carboxylic acid 24.4 g (77.5 mMol) 6-(2-amino-6-chloro-pyrimidin-4-yloxy)-naphthalene-1-carboxylic acid in 3.5 l THF and 100 ml Et$_3$N are hydrogenated in the presence of 15 g Pd/C (10%; Engelhard 4505). The catalyst is filtered off and washed extensively with THF. Partial concentration of the filtrate precipitates the title compound: MS: [M+1]$^+$=282.

Step 10:3: 6-(2-Amino-pyrimidin-4-yloxy)-naphthalene-1-carboxylic acid (4-fluoro-3-trifluoromethyl-phenyl)-amide To a suspension of 2.58 g (9.2 mMol) 6-(2-amino-pyrimidin-4-yloxy)-naphthalene-1-carboxylic acid in 50 ml DMF, 12.8 ml (92 mMol) Et$_3$N, 490 mg (4.0 mMol) DMAP, 1.41 ml (11 mMol) 4-fluoro-3-trifluoromethyl-aniline and finally 11 ml propylphosphonic anhydride (50% in DMF; 19 mMol) are added. The mixture is stirred for 1 h and then concentrated in vacuo. The residue is diluted with water and EtOAc, the aq. phase is separated off and extracted twice with EtOAc. The organic layers are washed with water and brine, dried (Na$_2$SO$_4$) and concentrated. Column chromatography (SiO$_2$; CH$_2$Cl$_2$/EtOAc 2:1→1:1→1:2) and re-crystallization from CH$_3$CN gives the title compound: m.p.: 205° C.

Example 11

{4-[5-(4-Fluoro-3-trifluoromethyl-phenylcarbamoyl)-naphthalen-2-yloxy]-pyrimidin-2-yl}carbamic acid isobutyl ester

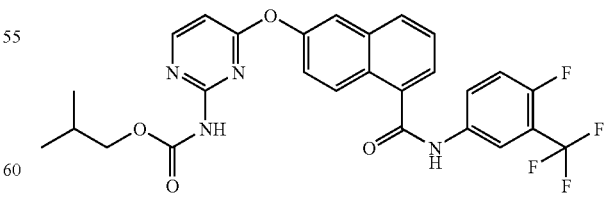

110 μl (0.84 mMol) isobutyl chloroformate are added portionwise to a solution of 300 mg (0.68 mMol) 6-(2-amino-pyrimidin-4-yloxy)-naphthalene-1-carboxylic acid (4-fluoro-3-trifluoromethyl-phenyl)-amide (Step 10.3) in 4.5 ml CH$_2$Cl$_2$ and 7.5 ml pyridine. After 1 h, the solution is

Example 12

6-(2-Acetylamino-pyrimidin-4-yloxy)-naphthalene-1-carboxylic acid (4-fluoro-3-trifluoromethyl-phenyl)-amide

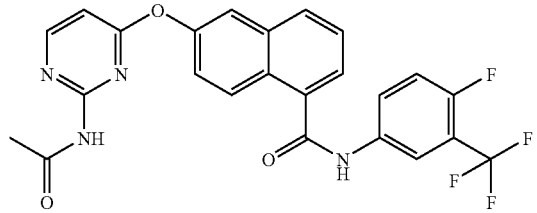

48 μl (0.68 mMol) acetyl chloride are added portionwise to a solution of 300 mg (0.68 mMol) 6-(2-amino-pyrimidin-4-yloxy)-naphthalene-1-carboxylic acid (4-fluoro-3-trifluoromethyl-phenyl)-amide (step 10.3) in 3.7 ml CH$_2$Cl$_2$ and 5.5 ml pyridine. After 1.5 h, the solution is diluted with EtOAc and water, the aq. phase separated off and extracted twice with EtOAc. The organic layers are washed with water and brine, dried (Na$_2$SO$_4$) and concentrated. Chromatography (Combi Flash; hexane/EtOAc 1:1→1:3) gives the title compound: m.p.: 213-214° C.

Example 13

6-(2-Methanesulfonylamino-pyrimidin-4-yloxy)-naphthalene-1-carboxylic acid (4-fluoro-3-trifluoromethyl-Phenyl)-amide

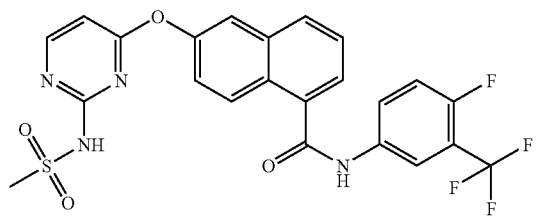

378 mg (2.17 mMol) methansulfonic acid anhydride are added in 3 portions to a solution of 300 mg (0.68 mMol) 6-(2-amino-pyrimidin-4-yloxy)-naphthalene-1-carboxylic acid (4-fluoro-3-trifluoromethyl-phenyl)-amide (Step 10.3) in 4.5 ml CH$_2$Cl$_2$ and 7.5 ml pyridine. After 20 h, the solution is diluted with EtOAc and water, the aq. phase separated off and extracted twice with EtOAc. The organic layers are washed with water and brine, dried (Na$_2$SO$_4$) and concentrated. Chromatography (Combi Flash; CH$_2$Cl$_2$-CH$_2$Cl$_2$/EtOH 19:1) gives the title compound: MS: [M+1]$^+$=543.

Chromatography (Combi Flash; CH$_2$Cl$_2$/THF 50:1-9:1) gives the title compound: m.p.: 246° C.; MS: [M−1]=519.

Example 14

6-[2-(3-Methyl-ureido)-pyrimidin-4-yloxy]-naphthalene-1-carboxylic acid (4-fluoro-3-trifluoromethyl-phenyl)-amide

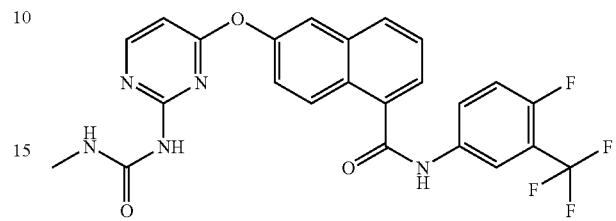

130 μl (2.2 mMol) methyl isocyanate are added to a solution of 300 mg (0.68 mMol) 6-(2-amino-pyrimidin-4-yloxy)-naphthalene-1-carboxylic acid (4-fluoro-3-trifluoromethyl-phenyl)-amide (Step 10.3) in 10 ml THF in a sealed vessel. The mixture is stirred at 100° C. for 11 days (another 1.1 eq. of Me-NCO is added on day 8 and 9). Then the reaction mixture is diluted with EtOAc and water, the aq. phase separated off and extracted twice with EtOAc. The organic layers are washed with water and brine, dried (Na$_2$SO$_4$) and partially concentrated. Precipitation with hexane, filtration and re-crystallization from boiling THF/CH$_3$CN gives the title compound: m.p.: 233-234° C.

Example 15

6-(2-Methoxymethyl-pyrimidin-4-yloxy)-naphthalene-1-carboxylic acid (3-cyclopropyl-phenyl)-amide

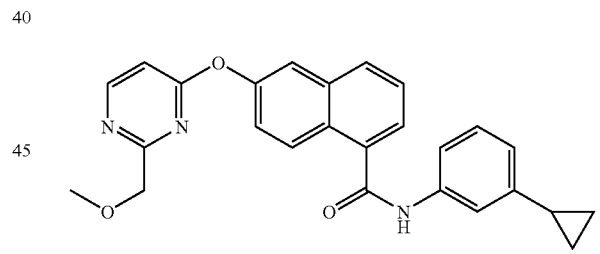

In a dried vessel, 32.8 mg (0.247 mMol) 3-cyclopropyl-aniline [preparation see: *Tet. Lett.* 43 (2002) 6987] are dissolved in 4.3 ml toluene and cooled to 10° C. Then 370 μl Me$_3$Al (2 M in toluene; 0.74 mMol) are added via syringe. After 1 h at rt, a solution of 80 mg (0.247 mMol) 6-(2-methoxymethyl-pyrimidin-4-yloxy)-naphthalene-1-carboxylic acid methyl ester (Step 15.4) in 1 ml THF is added and the reaction mixture is stirred for 30 min in an oil bath of 110° C. The solution is cooled in ice and hydrolyzed with 11 ml of a sat. NH$_4$Cl. After 15 min stirring, the mixture is diluted with EtOAc and water, the aq. phase separated off and extracted with EtOAc. The organic layers are washed with water and brine, dried (Na$_2$SO$_4$) and concentrated. Chromatography (Combi Flash; toluene/acetone 99:1→4:1) gives the title compound: MS: [M+1]$^+$=426; TLC (toluene/acetone 4:1): R$_f$=0.09.

The starting material is prepared as follows:

Step 15.1: 6-(6-Chloro-2-methyl-pyrimidin-4-yloxy)-naphthalene-1-carboxylic acid methyl ester A suspension of 6.0 g (29.7 mMol) 6-hydroxy-naphthalene-1-carboxylic acid methyl ester (see Step 3.1), 7.6 g (46.6 mMol) 4,6-dichloro-2-methylpyrimidine and 13.9 g (65 mMol) $K_3PO_4$ in 50 ml NMP is stirred for 4 days at rt. The mixture is poured into ½ l water and the title compound filtered off, washed with water and dried (HV, 80° C.): HPLC: $t_{Ret}$=17.2.

Step 15.2: 6-(2-Methyl-pyridin-4-yloxy)-naphthalene-1-carboxylic acid methyl ester 9.7 g (29.5 mMol) 6-(6-chloro-2-methyl-pyrimidin-4-yloxy)-naphthalene-1-carboxylic acid methyl ester in 950 ml THF and 24 ml (0.30 Mol) pyridine is hydrogenated in presence of 1.9 g Pd/C (10%, Engelhard 4505) during 15 h. The mixture is filtered, the solid washed extensively with THF and the filtrate concentrated. The residue is re-dissolved in EtOAc and 5% citric acid, the aq. layer separated off and extracted with EtOAc. The organic layers are washed with water and brine, dried ($Na_2SO_4$) and concentrated to the title compound: HPLC: $t_{Ret}$=12.8.

Step 15.3: 6-(2-Bromomethyl-pyrimidin-4-yloxy)-naphthalene-1-carboxylic acid methyl ester A solution of 8.55 g (29.05 mMol) 6-(2-methyl-pyrimidin-4-yloxy)-naphthalene-1-carboxylic acid methyl ester, 13.5 g N-bromo-succinimide (95%; 72.6 mMol) and 3.31 g (20 mMol) α,α-azoisobytyronitrile in 1.851 $CCl_4$ is heated to 80° C. and irradiated (125 W lamp) for 2 days. Then 5.44 g N-bromo-succinimide and 1.66 g α,α-azoisobytyronitrile are added and irradiation at 80° C. is continued for another day. The reaction mixture is concentrated, the residue re-dissolved in EtOAc and water, the aq. layer separated off and extracted with EtOAc. The organic layers are washed with water and brine, dried ($Na_2SO_4$) and concentrated. Column chromatography ($SiO_2$; hexane/EtOAc 1:1) gives the title compound: MS: $[M+1]^+$=373/375; TLC(hexane/EtOAc 1:1): $R_f$=0.35.

Step 15.4: 6-(2-Methoxymethyl-pyrimidin-4-yloxy)-naphthalene-1-carboxylic acid methyl ester 760 μl (4.12 mMol) of a 5.4 M solution of MeONa in MeOH are added to a solution of 1.28 g (3.43 mMol) 6-(2-bromomethyl-pyrimidin-4-yloxy)-naphthalene-1-carboxylic acid methyl ester in 70 ml MeOH. After 22 h stirring at rt, the mixture is diluted with EtOAc and water, the aq. layer separated off and extracted twice with EtOAc. The organic layers are washed with water and brine, dried ($Na_2SO_4$) and concentrated. Chromatography (Combi Flash; hexane/EtOAc 19: 1→1:3) gives the title compound: MS: $[M+1]^+$=325; $^1H$ NMR ($CDCl_3$): δ ppm 9.06 (d, 1H), 8.66 (d, 1H), 8.24 (d, 1H), 8.03 (d, 1H), 7.70 (s, 1H), 7.59 (t, 1H), 7.46 (d, 1H), 6.82 (d, 1H), 4.58 (s, $H_2C$), 4.06 (s, $H_3C$), 3.53 (s, $H_3C$).

Example 16

The Following Derivatives are Obtained Analogously to Ex. 15

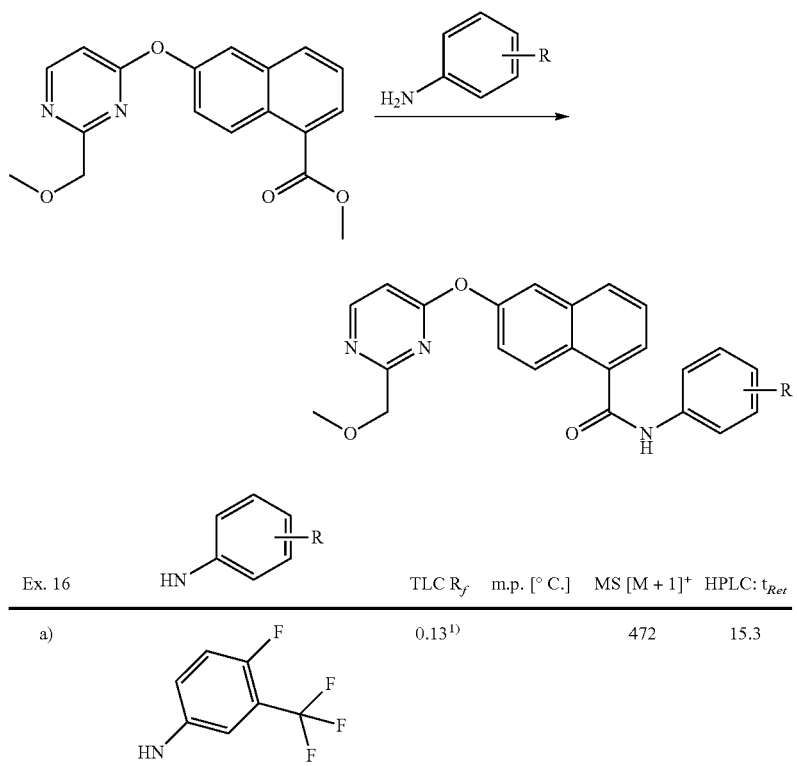

| Ex. 16 | | TLC $R_f$ | m.p. [° C.] | MS $[M + 1]^+$ | HPLC: $t_{Ret}$ |
|---|---|---|---|---|---|
| a) | | 0.13[1] | | 472 | 15.3 |

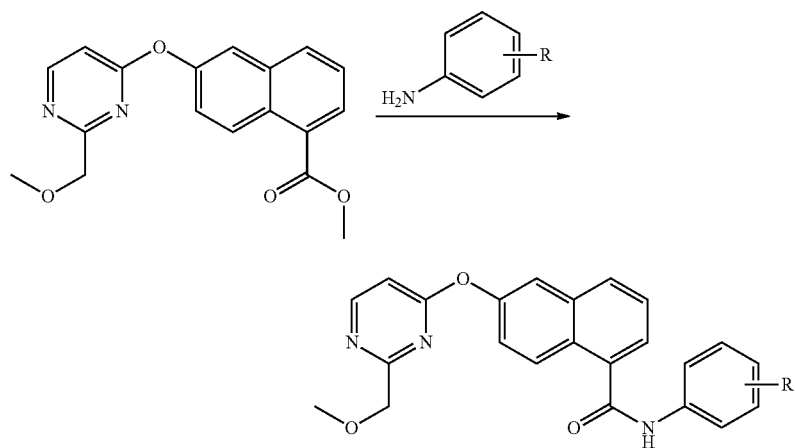
| Ex. 16 | HN—⟨⟩—R | TLC $R_f$ | m.p. [°C.] | MS [M + 1]$^+$ | HPLC: $t_{Ret}$ |
|---|---|---|---|---|---|
| b) | 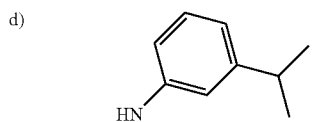 | 0.17[1)] | | 470 | 15.6 |
| c) | | 0.17[1)] | | 454 | 15.1 |
| d) | | | | | |
| e) | | 0.19[1)] | | 414 | |
| f) | 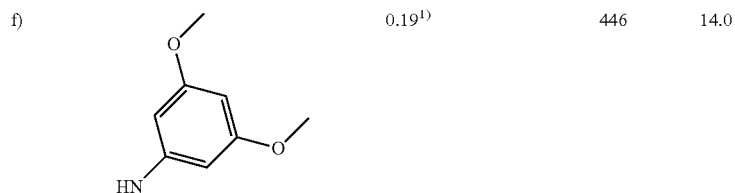 | 0.19[1)] | | 446 | 14.0 |

-continued
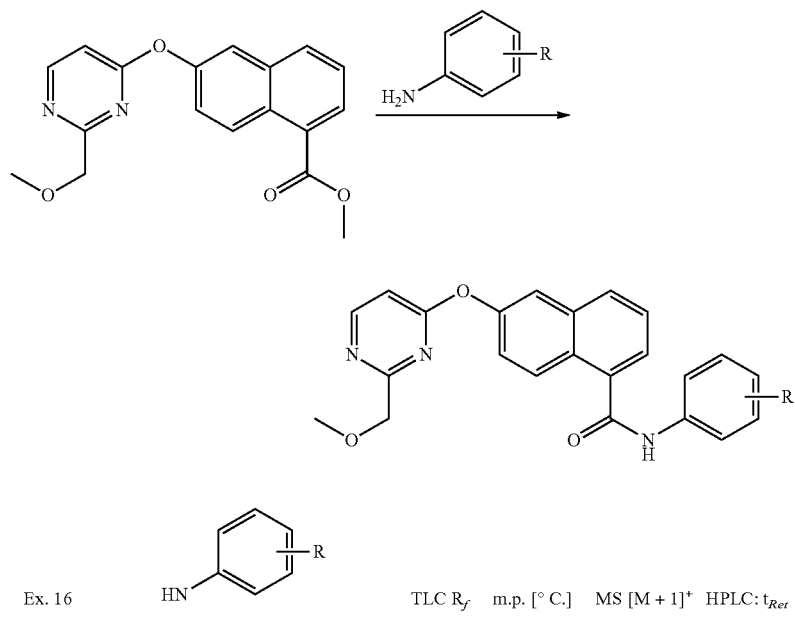
| Ex. 16 | | TLC R_f | m.p. [° C.] | MS [M + 1]⁺ | HPLC: t_Ret |
|---|---|---|---|---|---|
| g) | 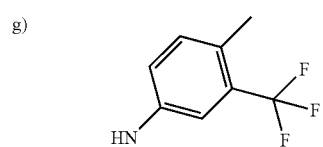 | | | | |
| h) | 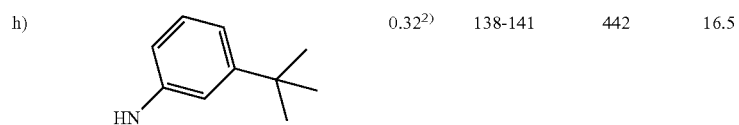 | 0.32[2)] | 138-141 | 442 | 16.5 |
| i) | 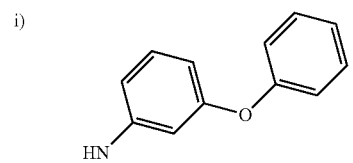 | | | | |
| j) | 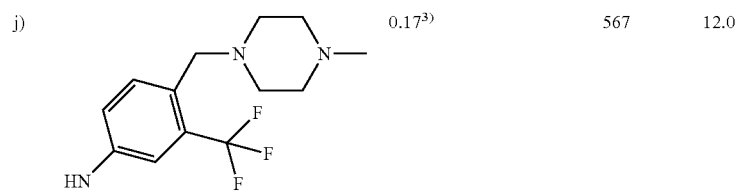 | 0.17[3)] | | 567 | 12.0 |
[1)]toluene/acetone 4:1;
[2)]toluene/acetone 7:3;
[3)]EtOAc/EtOH/$^{conc}$NH$_3$$^{aq}$·50:50:1

Example 17

4-[5-(4-Fluoro-3-trifluoromethyl-phenylcarbamoyl)-naphthalen-2-yloxy]-pyrimidine-2-carboxylic acid ethyl ester

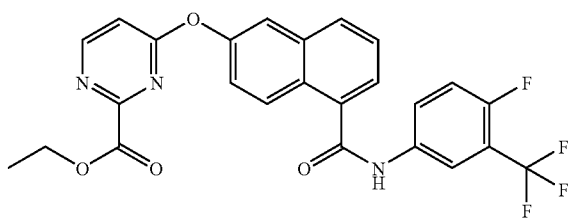

To a solution of 242 mg (0.717 mMol) 4-(5-carboxy-naphthalen-2-yloxy)-pyrimidine-2-carboxylic acid ethyl ester in 10.7 ml DMF, 1.5 ml (10.8 mMol) Et$_3$N, 38 mg (0.31 mMol) DMAP, 111 µl (0.86 mMol) 5-amino-2-fluorobenzotrifluoride and 880 µl propylphosphonic anhydride (50% in DMF; 1.5 mMol) are added. After 30 min stirring, the reaction mixture is diluted with water and EtOAc, the aq. phase separated off and extracted twice with EtOAc. The organic layers are washed with water and brine, dried (Na$_2$SO$_4$) and concentrated. Chromatography (Combi Flash; CH$_2$Cl$_2$→CH$_2$Cl$_2$/acetone 19:1) gives the title compound: MS: [M+1]$^+$=500; TLC (CH$_2$Cl$_2$/acetone 9:1): R$_f$=0.54.

The starting material is prepared as follows:

Step 17.1: 6-(2-Chloro-pyrimidin-4-yloxy)-naphthalene-1-carboxylic acid

To a mixture of 7.4 g (39.5 mMol) 6-hydroxy-1-naphthoic acid and 5.9 g (39.5 mMol) 2,4-dichloropyrimidin in 104 ml of acetone, 79 ml NaOH (1 M in H$_2$O) are added dropwise. The mixture is stirred for 19 h at rt and finally 2 h at 50° C. Then it is poured into 1.3 l water and acidified by addition of 40 ml of a 2 M HCl solution. Filtration of the suspension, washing with water and drying gives the title compound: MS: [M+1]$^+$=301.

Step 17.2: 4-(5-Carboxy-naphthalen-2-yloxy)-pyrimidine-2-carboxylic acid ethyl ester A mixture of 5 g (16.6 mMol) 6-(2-chloro-pyrimidin-4-yloxy)-naphthalene-1-carboxylic acid, 80 ml EtOH, 7 ml (50 mMol) Et$_3$N and 1180 mg (1.6 mMol) PdCl$_2$(PPh$_3$)$_2$ is stirred under a atmosphere of 120 bar carbonmonoxide in an autoclave for 12 h at 115° C. The reaction mixture is diluted with 500 ml EtOAc and 500 ml 10% citric acid. The aq. layer is separated off and extracted with 2 Portions of EtOAc. The organic phases are washed with water and brine, dried (Na$_2$SO$_4$) and concentrated. Trituration of the residue in EtOAc and filtration gives the title compound. More product can be isolated from the filtrate by chromatography (Combi Flash; CH$_2$Cl$_2$/EtOAc 4:1→EtOAc): m.p.: 214-217° C.; MS: [M+1]$^+$=339; TLC(EtOAc+0.5% HOAc): R$_f$=0.30.

Example 17A 6-(2-Hydroxymethyl-pyrimidin-4-yloxy)-naphthalene-1-carboxylic acid (4-fluoro-3-trifluoromethyl-phenyl)-amide

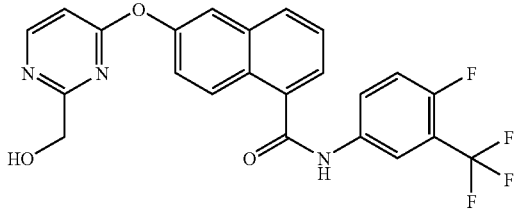

To a suspension of 523 mg (1.048 mMol) 4-[5-(4-fluoro-3-trifluoromethyl-phenylcarbamoyl)-naphthalen-2-yloxy]-pyrimidine-2-carboxylic acid ethyl ester in 13.8 ml tert-butanol, 119 mg (3.14 mMol) NaBH$_4$ are added. This mixture is stirred for 2 h at 70° C. and then concentrated in vacuo. The residue is diluted with water and EtOAc, the aq. phase separated off and extracted twice with EtOAc. The organic layers are washed with brine, dried (Na$_2$SO$_4$) and concentrated. Chromatography [Combi Flash; CH$_2$Cl$_2$/(CH$_2$Cl$_2$/$^{tert}$BuOH 1:1) 99:1→83:17] and trituration from DIPE gives the title compound: Anal. (+0.3H$_2$O+0.4 DIPE): C, H, N, F; MS: [M+1]$^+$=458; TLC (CH$_2$Cl$_2$/acetone 9:1): R$_f$=0.44.

Example 17B
The Following Derivatives are Obtained Analogously to Ex. 17 and 17A
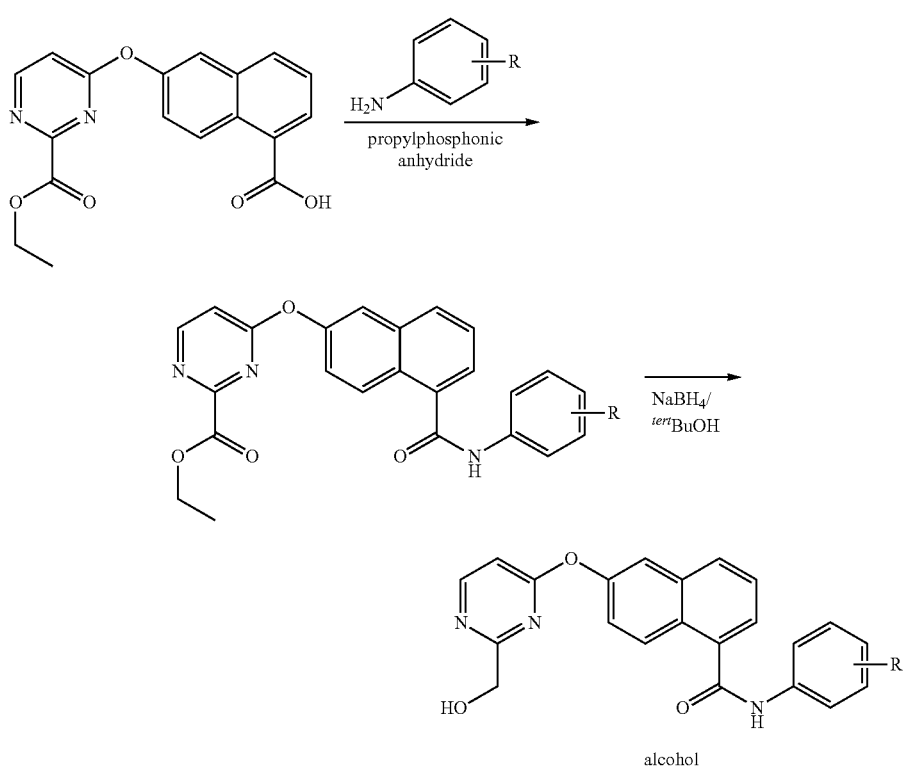
| Ex. 17B. |  | TLC R_f | m.p. [° C.] | MS [M + 1]⁺ | HPLC: t_{Ret} | Anal. |
|---|---|---|---|---|---|---|
| a) ester alcohol | 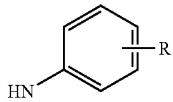 | 0.40¹⁾<br>0.23³⁾ |  | 470<br>428 | 17.4<br>15.1 |  |
| b) ester alcohol | 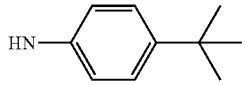 | 0.52¹⁾<br>0.26³⁾ |  | 498<br>456 | 16.6 |  |
| c) ester alcohol | 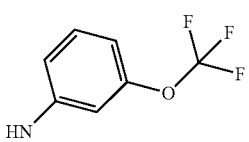 | 0.35¹⁾<br>0.38²⁾ | 204-207 | 482<br>440 | 16.1 | C, H, N, F |
| d) ester alcohol | 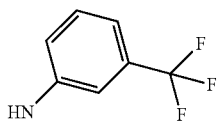 |  |  |  |  |  |

| | | | | |
|---|---|---|---|---|
| e) ester alcohol | ![structure] | | | |
| f) ester alcohol | ![structure] | | | |
| g) ester alcohol | ![structure] | 0.46[1]) 0.58[4]) | 454 412 | 16.3 13.7 |
| h) ester alcohol | ![structure] | | 595 553 | 13.3 11.2 |

[1]) $CH_2Cl_2$/acetone 9:1;
[2]) $CH_2Cl_2$/acetone 2:5;
[3]) $CH_2Cl_2$/acetone/HOAc 4:1:0.02;
[4]) $CH_2Cl_2$/$^{tert}$BuOH/HOAc 4:1:0.02

Example 18

6-[5-(4-tert-Butyl-phenylcarbamoyl-naphthalen-2-yloxy]-pyrimidine-4-carboxylic acid ethyl ester

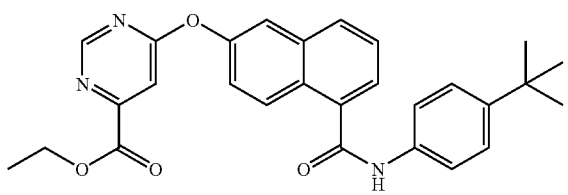

To a solution of 500 mg (1.48 mMol) 6-(5-carboxy-naphthalen-2-yloxy)-pyrimidine-4-carboxylic acid ethyl ester in 2 ml DMF, 3.09 ml (22.2 mMol) $Et_3N$, 264 mg (1.77 mMol) 4-tert-butylaniline and 1.8 ml propylphosphonic anhydride (50% in DMF; 3.08 mMol) are added. The yellowish solution is stirred for 2 h at rt and then poured into a mixture of ice-water, sat. $NaHCO_3$ and EtOAc. After 15 min stirring, the aq. phase is separated off and extracted twice with EtOAc. The organic layers are washed 3 times with water and brine, dried ($Na_2SO_4$) and concentrated. Chromatography ($SiO_2$; $CH_2Cl_2$/acetone 19:1) and trituration in hexane gives the title compound: m.p.: 177-178° C.; Anal. (+0.3$H_2O$+0.4 DIPE): C, H, N, O; MS: [M+1]$^+$=470; TLC ($CH_2Cl_2$/acetone 19:1): $R_f$=0.24.

The starting material is prepared as follows:

Step 18.1: 6-(5-Carboxy-naphthalen-2-yloxy)-pyrimidine-4-carboxylic acid ethyl ester A mixture of 10 g (33.3 mMol) 6-(6-chloro-pyrimidin-4-yloxy)-naphthalene-1-carboxylic acid (preparation see WO 2006/59234; Step 25.1), 150 ml EtOH, 9.03 ml (64:9 mMol) $Et_3N$ and 2.35 g (3.32 mMol) $PdCl_2(PPh_3)_2$ is stirred under a atmosphere of 120 bar carbonmonoxide in an autoclave for 12 h at 115° C. The reaction mixture is diluted with 400 ml EtOAc, filtered through Hyflo and the residue washed with MeOH. The filtrate is concentrated and the residue suspended in 400 ml EtOAc and 200 ml water. Acidification to pH 4 with 4 N HCl and addition of MeOH produces a solution. The aq. layer is separated off and extracted with 3 portions of EtOAc. The organic phases are washed with water and brine, dried ($Na_2SO_4$), treated with char coal and concentrated. Trituration of the residue in EtOAc/ether and filtration gives the title compound: m.p.: 211-212° C.; MS: [M+1]$^+$=339.

Example 18A 6-(6-Hydroxymethyl-pyrimidin-4-yloxy)-naphthalene-1-carboxylic acid (4-tert-butyl-phenyl)-amide

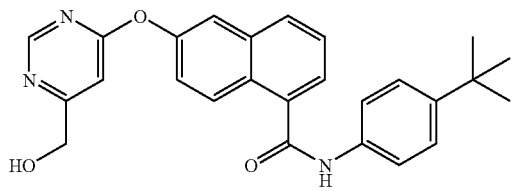

To a suspension of 224 mg (0.477 mMol) 6-[5-(4-tert-butyl-phenylcarbamoyl-naphthalen-2-yloxy]-pyrimidine-4-carboxylic acid ethyl ester in 5 ml tert-butanol, 54 mg (1.43 mMol) NaBH$_4$ are added. After stirring for 50 min at 60° C., the yellowish suspension is diluted with water and EtOAc, the aq. phase separated off and extracted twice with EtOAc. The organic layers are washed with water and brine, dried (Na$_2$SO$_4$) and concentrated. Chromatography (SiO$_2$; EtOAc) and trituration from hexane gives the title compound: m.p.: 202-203° C.; Anal. (+0.4H$_2$O): C, H, N, O; MS: [M+1]$^+$=428;

$^1$H-NMR (DMSO-d$_6$): δ ppm 10.52 (s, HN), 8.65 (s, 1H), 8.25 (d, 1H), 8.06 (d, 1H), 7.87 (s, 1H), 7.72 (m, 3H), 7.64 (t, 1H), 7.48 (d, 1H), 7.38 (d, 2H), 7.10 (s, 1H), 5.66 (t, HO), 4.56 (d, H$_2$C), 1.30 (s, 9H).

Example 18B

The Following Derivatives are Obtained Analogously to Ex. 18 and 18A

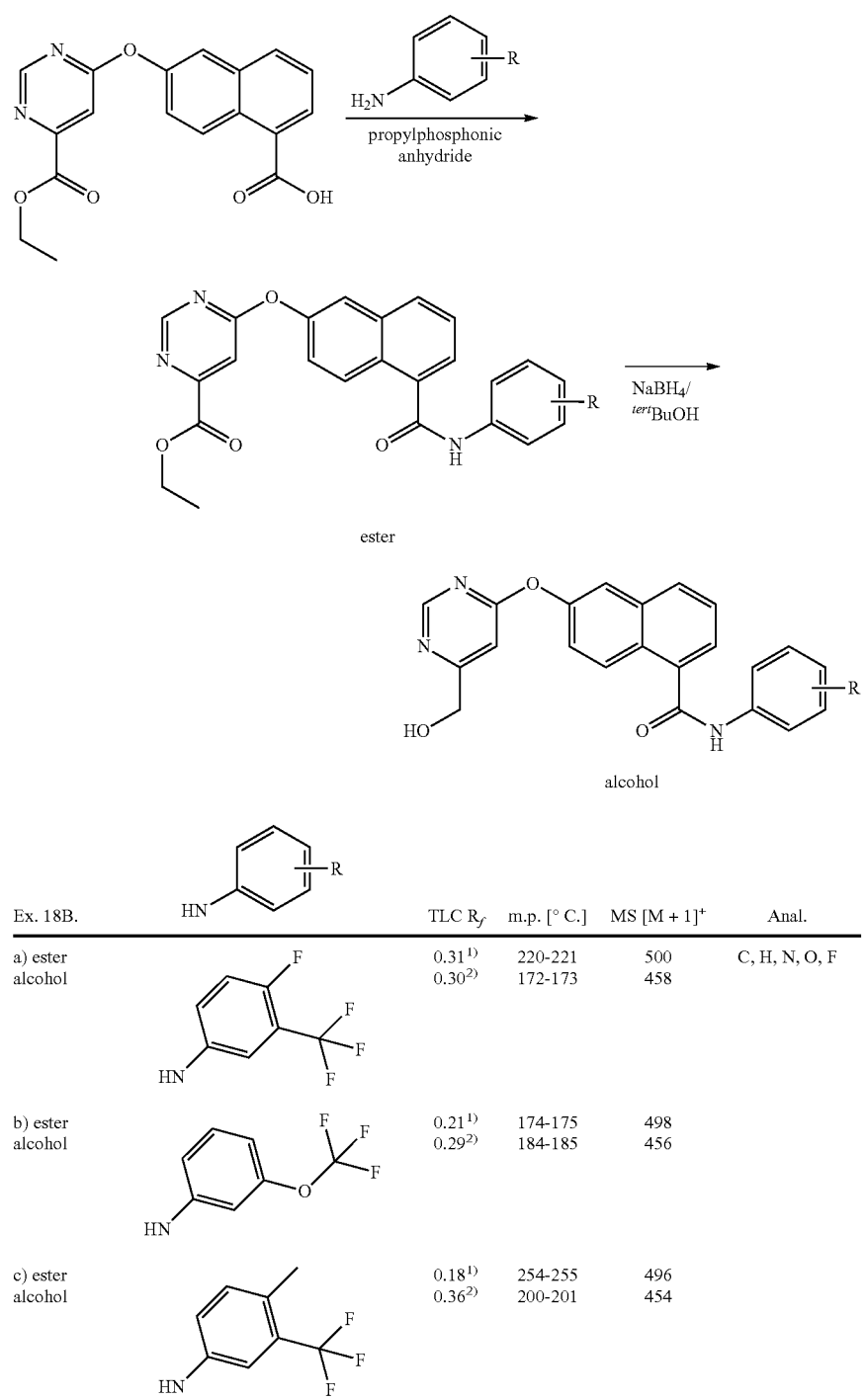

| Ex. 18B. | HN-Ph-R | TLC R$_f$ | m.p. [° C.] | MS [M + 1]$^+$ | Anal. |
|---|---|---|---|---|---|
| a) ester | 4-F, 3-CF$_3$ aniline | 0.31$^{1)}$ | 220-221 | 500 | C, H, N, O, F |
| alcohol | | 0.30$^{2)}$ | 172-173 | 458 | |
| b) ester | 3-OCF$_3$ aniline | 0.21$^{1)}$ | 174-175 | 498 | |
| alcohol | | 0.29$^{2)}$ | 184-185 | 456 | |
| c) ester | 4-Me, 3-CF$_3$ aniline | 0.18$^{1)}$ | 254-255 | 496 | |
| alcohol | | 0.36$^{2)}$ | 200-201 | 454 | |

| | | | | | |
|---|---|---|---|---|---|
| d) ester alcohol | 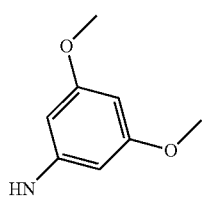 | | | | |
| e) ester alcohol | 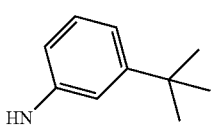 | 0.26[1) 0.32[2) | 171-172 170-171 | 470 428 | C, H, N, O |
| f) ester alcohol | 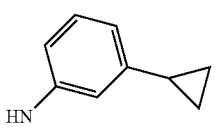 | 0.16[1) 0.28[2) | 143-144 192-193 | 454 412 | C, H, N, O |
| g) ester alcohol | 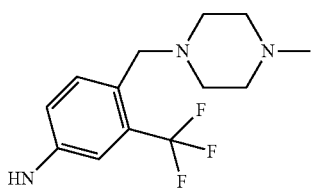 | | | | |
| h) ester alcohol | 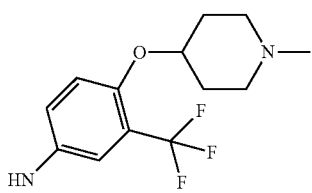 | 0.37[3) 0.23[3) | 180-181 | 595 553 | |
| i) ester alcohol | 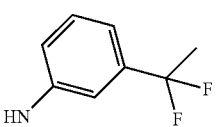 | 0.23[1) 0.36[2 | 176-177 201-202 | 478 436 | C, H, N, O |
| j) ester alcohol | 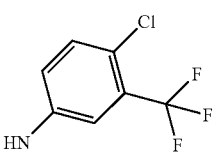 | 0.23[1) 0.38[2 | 252-253 164-165 | 516/519 474/476 | C, H, N, Cl, FO C, H, N, Cl, FO |
[1)]$CH_2Cl_2$/acetone 19:1;
[2)]EtOAc;
[3)]$CH_2Cl_2$/MeOH/$^{conc}NH_3^{aq}$ 90:10:1

Example 18C 6-(6-Methoxymethyl-pyrimidin-4-yloxy)-naphthalene-1-carboxylic acid (4-methyl-3-trifluoromethyl-phenyl)-amide

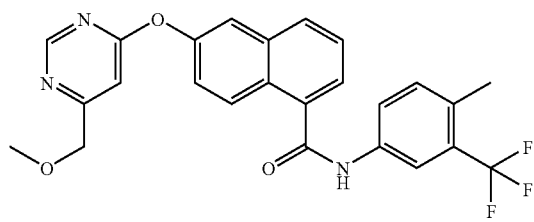

In a dried vessel, 68 mg (0.388 mMol) 5-amino-2-methyl-benzotrifluoride are dissolved in 7 ml toluene and cooled in an ice bath. Then 580 µl Me$_3$Al (2 M in toluene; 1.16 mMol) are added via syringe. After 1 h at rt, a solution of 126 mg (0.388 mMol) 6-(6-methoxymethyl-pyrimidin-4-yloxy)-naphthalene-1-carboxylic acid methyl ester in 1.5 ml THF is added and the solution is stirred for ½ h in an oil bath of 110° C. The solution is cooled in an ice bath and hydrolyzed with 13 ml of a sat. NH$_4$Cl solution. After 15 min stirring, the mixture is diluted with EtOAc and water, the aq. phase separated off and extracted twice with EtOAc. The organic layers are washed with water and brine, dried (Na$_2$SO$_4$) and concentrated. Chromatography (Combi Flash; CH$_2$Cl$_2$/acetone 99:1→19:1) and crystallization from DIPE/hexane gives the title compound: m.p.: 188° C.; Anal.: C, H, N, F; MS: [M+1]$^+$=468; TLC (CH$_2$Cl$_2$/acetone 9:1): R$_f$=0.32; $^1$H-NMR (DMSO-d$_6$): δ ppm 10.85 (s, HN), 8.69 (s, 1H), 8.28 (d, 1H), 8.24 (s, 1H), 8.10 (d, 1H), 7.93 (d, 1H), 7.90 (s, 1H), 7.80 (d, 1H), 7.66 (t, 1H), 7.48 (d, 1H), 7.44 (d, 1H), 7.07 (s, 1H), 4.50 (s, H$_2$C), 3.4 (s, H$_3$C), 2.43 (s, H$_3$C).

The starting material is prepared as follows:

Step 18C.1: 6-(6-Methoxymethyl-pyrimidin-4-yloxy)-naphthalene-1-carboxylic acid methyl ester A suspension of 3.4 g (16.8 mMol) 6-hydroxy-naphthalene-1-carboxylic acid methyl ester (see Step 3.1), 3.2 g (20.2 mMol) 4-chloro-6-(methoxymethyl)pyrimidine (preparation see: BE 64 1253, p. 38; or WO 2002/45652, p. 102) and 7.85 g (37 mMol) K$_3$PO$_4$ in 85 ml NMP is stirred for 4 h at 90° C. The cooled mixture is diluted with 0.4 l EtOAc and 0.4 l water, the aq. phase separated off and extracted twice with EtOAc. The organic layers are washed twice with water and brine, dried (Na$_2$SO$_4$) and concentrated. Chromatography (SiO$_2$; CH$_2$Cl$_2$/EtOAc 19:1→9:1→4:1) gives the title compound: m.p.: 87-88° C.; MS: [M+1]$^+$=325; TLC (CH$_2$Cl$_2$/EtOAc 4:1): R$_f$=0.28.

Example 18D

The Following Derivatives are Obtained Analogously to Ex. 18C

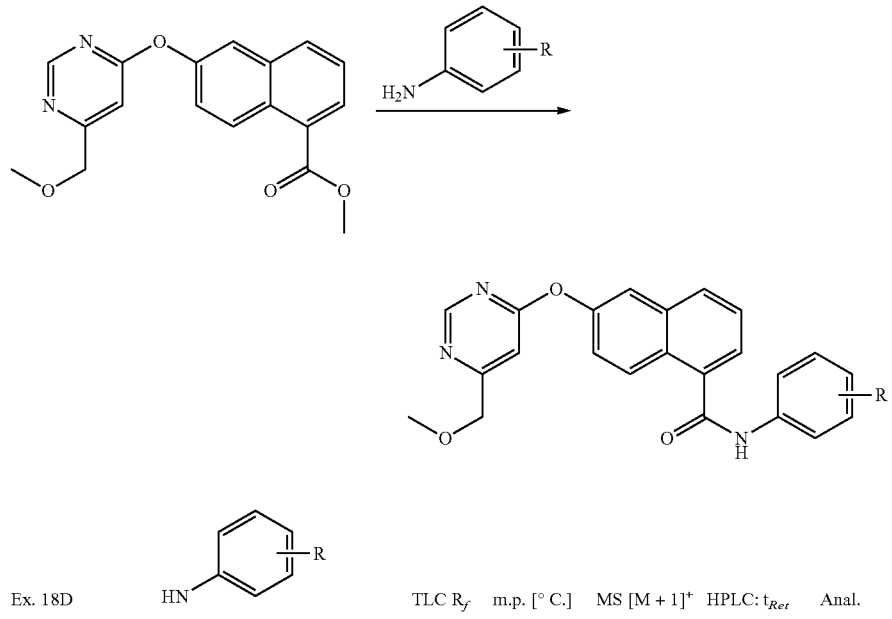

| Ex. 18D | HN-Ar | TLC R$_f$ | m.p. [° C.] | MS [M + 1]$^+$ | HPLC: t$_{Ret}$ | Anal. |
|---|---|---|---|---|---|---|
| a) | 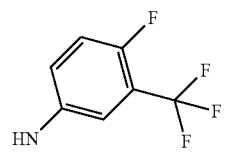 | | | | | |

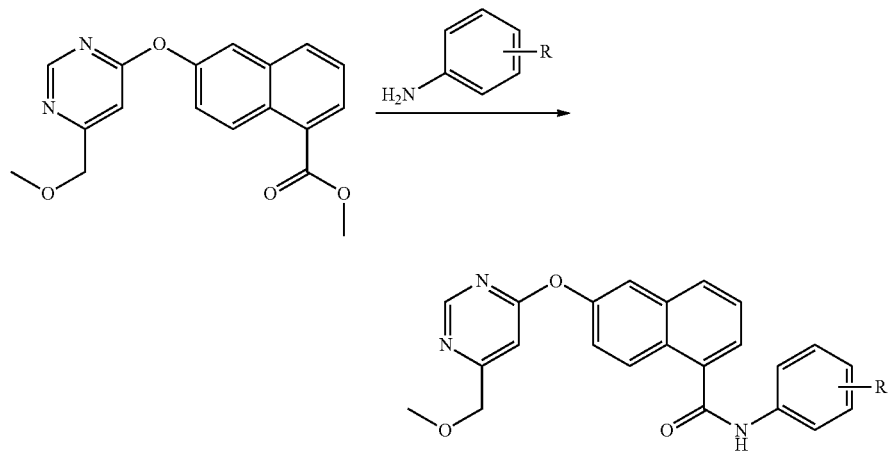
| Ex. 18D | | TLC $R_f$ | m.p. [° C.] | MS [M + 1]$^+$ | HPLC: $t_{Ret}$ | Anal. |
|---|---|---|---|---|---|---|
| b) | 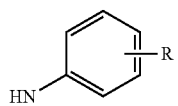 | 0.33$^{2)}$ | 177 | 470 | 17.0 | C, H, N, F |
| c) | 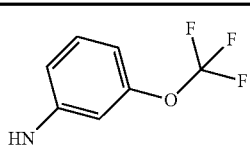 | 0.22$^{1)}$ | 165-168 | 454 | 16.8 | C, H, N, F |
| d) | 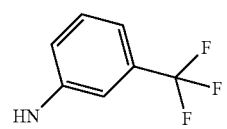 | | | | | |
| e) | 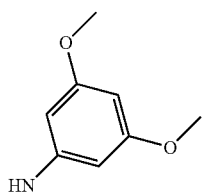 | 0.33$^{2)}$ | 159 | 442 | 16.6 | C, H, N |
| f) | 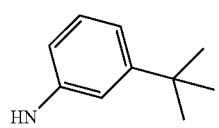 | | | | | |
| g) | 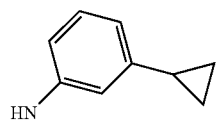 | | | | | |

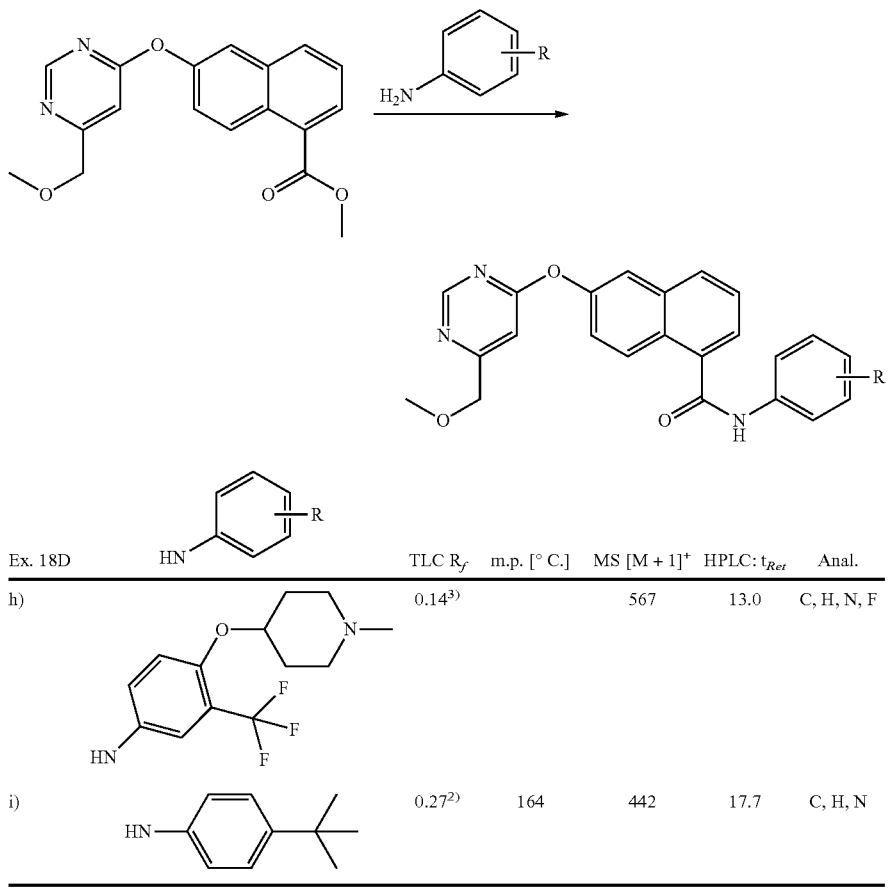

| Ex. 18D | HN-[phenyl-R] | TLC R_f | m.p. [° C.] | MS [M + 1]⁺ | HPLC: t_Ret | Anal. |
|---|---|---|---|---|---|---|
| h) | | 0.14³⁾ | | 567 | 13.0 | C, H, N, F |
| i) | | 0.27²⁾ | 164 | 442 | 17.7 | C, H, N |

¹⁾CH₂Cl₂/EtOAc 4:1;
²⁾CH₂Cl₂/acetone 9:1;
³⁾CH₂Cl₂/THF/conc.NH₃ aq. 25:25:1

Example 19

6-[6-(2-Dimethylamino-ethylamino)-pyrimidin-4-yloxy]-naphtalene-1-carboxylic acid [5-tert-butyl-2-(4-methoxy-phenyl)-2H-pyrazol-3-yl]-amide

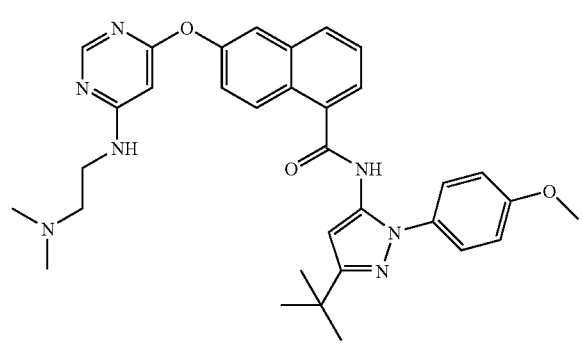

220 mg (0.41 mMol) 6-(6-Chloro-pyrimidin-4-yloxy)-naphthalene-1-carboxylic acid [5-tert-butyl-2-(4-methoxy-phenyl)-2H-pyrazol-3-yl]-amide and 91 µl (0.83 mMol) 2-N,N-dimethylamino ethylamine are dissolved in 5 ml CH₂Cl₂. The reaction mixture is stirred at 40° C. for 30 h. It is worked up by removal of all volatiles under reduced pressure. The remaining crude product is purified by flash chromatography (combi-flash: 14 g column, CH₂Cl₂/MeOH; gradient 1-15% MeOH) to give the title compound as a yellow solid: m.p.: 116-117° C.; MS: [M+1]⁺=581.

The starting material is prepared as follows:

Step 19.1: 5-tert-Butyl-2-(4-methoxy-phenyl)-2H-pyrazol-3-ylamine

The title compound is prepared according to a published literature procedure (see *J. Med. Chem.* 2002, 45, 2994-3008): 3.9 g (31.5 mMol) of pivaloylacetonenitrile are added to a solution of 5.5 g (31.5 mMol) 4-methoxyphenylhydrazine in 50 ml of toluene at rt, and the resulting yellow solution is heated to and kept under reflux for 12 h. After completion the reaction mixture is concentrated and dried to give the title compound as a yellow solid: MS: [M+1]⁺=246.

Step 19.2: 6-(6-Chloro-pyrimidin-4-yloxy)-naphthalene-1-carboxylic acid [5-tert-butyl-2-(4-methoxy-phenyl)-2H-pyrazol-3-yl]-amide 2.9 g (12 mMol) 5-tert-butyl-2-(4-methoxy-phenyl)-2H-pyrazol-3-ylamine and 3.8 g (12 mMol) 6-(6-chloropyrimidin-4-yloxy)-naphthalene-1-carbonyl chloride (described under Step 19.3) are dissolved in 10 ml CH₂Cl₂ and cooled to 0° C. 0.99 ml (12 mMol) Pyridine are added dropwise and after complete addition the reaction is allowed to warm to rt. It is stirred for 2 h at ambient temperature. The reaction is worked up by addition of 150 ml CH$_2$Cl$_2$ and aq. extraction with sat. Na$_2$CO$_3$ solution. The organic layer is subsequently washed with brine and dried. After removal of the solvents the remaining crude product is purified by flash chromatography (SiO$_2$; hexanes/EtOAc, gradient 3:1 to 2:1) to give the title compound as a yellow solid: m.p.: 163-164° C.

Step 19.3: 6-(6-Chloropyrimidin-4-yloxy)-naphthalene-1-carbonyl chloride

A solution of 571 µl (6.66 mMol) oxalyl chloride in 15 ml CH$_2$Cl$_2$ is added to an ice-cooled solution of 1 g (3.33 mMol) 6-(6-chloro-pyrimidin-4-yloxy)-naphthalene-1-carboxylic acid (preparation see WO 2006/59234; Step 25.1) and 10 µl DMF in 30 ml CH$_2$Cl$_2$. The reaction mixture is stirred at room temperature for 1 h. The solvent is then evaporated off under reduced pressure to afford the title compound as a brown solid, which is used directly without further purification.

Example 20

6-[6-(2-Dimethylamino-ethylamino)-pyrimidin-4-yloxy]-naphtalene-1-carboxylic acid [5-tert-butyl-2-(4-fluoro-phenyl)-2H-pyrazol-3-yl]amide

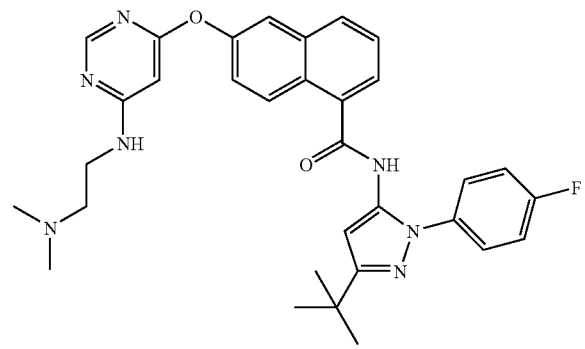

100 mg (0.2 mMol) 6-(6-chloro-pyrimidin-4-yloxy)-naphthalene-1-carboxylic acid [5-tert-butyl-2-(4-fluoro-phenyl)-2H-pyrazol-3-yl]-amide and 47 µl (0.46 mMol) 2-N,N-dimethylamino ethylamine are dissolved in 5 ml EtOH. The reaction mixture is stirred at reflux for 30 h. It is worked up by removal of all volatiles under reduced pressure. The remaining crude product is purified by flash chromatography (combi-flash: 14 g column, CH$_2$Cl$_2$/MeOH; gradient 1-15% MeOH) to give the title compound as a yellow solid: m.p.: 153-155° C.

The starting material is prepared as follows:

Step 20.1: 5-tert-Butyl-2-(4-fluoro-phenyl)-2H-pyrazol-3-ylamine

The title compound is prepared according to a published literature procedure (see *J. Med. Chem.* 2002, 45, 2994-3008.): 4.17 g (32.3 mMol) of pivaloylacetonitrile are added to a solution of 4.20 g (32.3 mMol) 4-fluoro-phenylhydrazine in 150 ml of toluene at rt, and the resulting yellow solution is heated to and kept under reflux for 12 h. After completion, the reaction mixture is concentrated, and the resulting crude product is purified by flash chromatography (SiO$_2$, 100% CH$_2$Cl$_2$) to give the title compound as a yellow solid: $^1$HNMR (CDCl$_3$) δ ppm 7.59 (d, 2H), 7.10 (d, 2H), 5.58 (s, 1H), 3.62 (brs, H$_2$N), 1.32 (s, 9H).

Step 20.2: 6-(6-Chloro-pyrimidin-4-yloxy)-naphthalene-1-carboxylic acid [5-tert-butyl-2-(4-fluoro-phenyl)-2H-pyrazol-3-yl]-amide 560 mg (2.4 mMol) 5-tert-butyl-2-(4-fluoro-phenyl)-2H-pyrazol-3-ylamine and 763 mg (2.4 mMol) 6-(6-chloropyrimidin-4-yloxy)-naphthalene-1-carbonyl chloride (see Step 19.3) are dissolved in 5 ml CH$_2$Cl$_2$ and cooled to 0° C. 193 µl (2.4 mMol) Pyridine are added dropwise and after complete addition the reaction is allowed to warm to rt. It is stirred for 2 h at ambient temperature. The reaction is concentrated under reduced pressure and the remaining crude product is purified by flash chromatography (combi-flash, 40 g column; CH$_2$Cl$_2$/MeOH; gradient 0-5% MeOH) to give the title compound as a yellow foam: MS: [M+1]$^+$=517.

Example 21

6-[6-(2-Dimethylamino-propylamino)-pyrimidin-4-yloxy]-naphtalene-1-carboxylic acid [5-tert-butyl-2-(4-fluoro-phenyl)-2H-pyrazol-3-yl]-amide

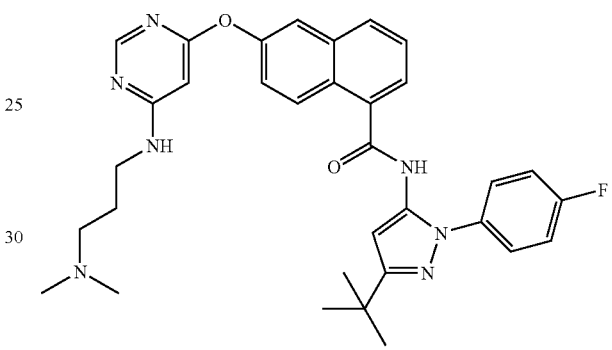

105 mg (0.20 mMol) 6-(6-Chloro-pyrimidin-4-yloxy)-naphthalene-1-carboxylic acid [5-tert-butyl-2-(4-fluoro-phenyl)-2H-pyrazol-3-yl]-amide (Step 20.1) and 42 mg (0.42 mMol) 2-N,N-dimethylamino propylamine are dissolved in 5 ml EtOH. The reaction mixture is stirred at reflux for 30 h. It is worked up by removal of all volatiles under reduced pressure. The remaining crude product is purified by flash chromatography (combi-flash: 14 g column, CH$_2$Cl$_2$/MeOH; gradient 1-15% MeOH) to give the title compound as a yellow solid: m.p.: 190-193° C.

Example 22

6-[6-[3-(4-Methyl-piperazin-1yl)-propylamino]-pyrimidin-4-yloxy]-naphtalene-1-carboxylic acid [5-tert-butyl-2-(4-fluoro-phenyl)-2H-pyrazol-3-yl]-amide

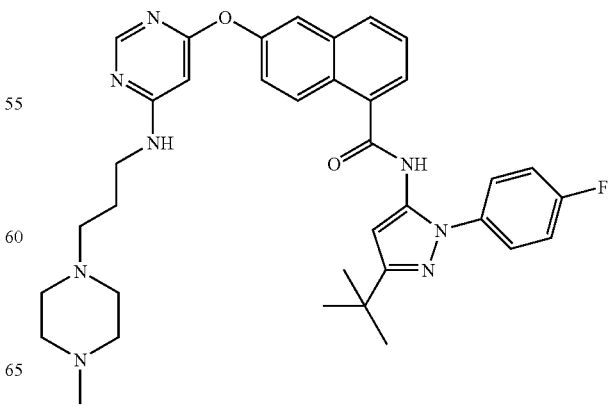

100 mg (0.19 mMol) 6-(6-Chloro-pyrimidin-4-yloxy)-naphthalene-1-carboxylic acid [5-tert-butyl-2-(4-fluoro-phenyl)-2H-pyrazol-3-yl]-amide (Step 20.1) and 73 μl (0.42 mMol) 1-(3-aminopropyl)-4-methylpiperazine are dissolved in 5 ml EtOH. The reaction mixture is stirred at reflux for 30 h. It is worked up by removal of all volatiles under reduced pressure. The remaining crude product is purified by flash chromatography (combi-flash: 14 g column, $CH_2Cl_2$/MeOH; gradient 0-20% MeOH) to give the title compound as a yellow solid: m.p.: 131-133° C.

Example 23

6-(6-Acetylamino-pyrimidin-4-yloxy)-isoquinoline-1-carboxylic acid [5-tert-butyl-2-(4-methoxy-phenyl)-2H-pyrazol-3-yl]-amide

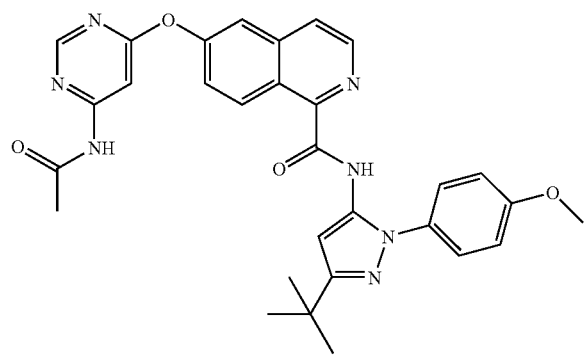

150.0 mg (0.28 mMol) 6-(6-Chloro-pyrimidin-4-yloxy)-isoquinoline-1-carboxylic acid [5-tert-butyl-2-(4-methoxy-phenyl)-2H-pyrazol-3-yl]-amide is dissolved in 5 ml dioxane. After addition of 131 mg $Cs_2CO_3$ (>99%, Fluka 20959; 0.40 mMol), 25 mg (0.43 mMol) acetamide, 20 mg Xantphos (Aldrich 52, 646-0; 0.034 mMol) and 10.5 mg $Pd_2(dba)_3$ (Aldrich 32, 877-4; 0.011 mMol) the reaction mixture is heated to 70° C. for 20 h. It is cooled to rt again and worked up by addition of $H_2O$ and EtOAc. The phases are separated and the aq. layer is repeatedly extracted with EtOAc. Combined organic extracts are washed with brine, dried and concentrated. The residual crude product is purified by flash chromatography (combi-flash: 40 g column, hexanes/EtOAc; gradient 0-50% EtOAc) to give the title compound as a yellow solid: MS: $[M+1]^+$=553; $^1$H MNR ($CDCl_3$): δ ppm 10.70 (s, 1H), 9.43 (d, 1H), 8.44 (s, 1H), 8.38 (d, 1H), 8.15 (bs, HN), 7.84 (s, 1H), 7.74 (d, 1H), 7.63 (s, 1H), 7.52-7.48 (m, 3H), 7.05 (d, 2H), 6.87 (s, 1H), 5.29 (s, 1H), 3.88 (s, 3H), 2.25 (s, 3H), 1.41 (s, 9H).

The starting material is prepared as follows:

Step 23.1: 6-(6-Chloro-pyrimidin-4-yloxy)-isoquinoline-1-carboxylic acid 40 ml (20 mMol) of a 0.5 M solution of sodium methylate in MeOH are added to a suspension of 1.9 g (10 mMol) 6-hydroxy-isoquinoline-1-carboxylic acid (CAS 174299-07-1) in 50 ml MeOH and sonicated until a solution is obtained. The solvent is then evaporated off. The residue is dried in high vacuum for 4 h and 100 ml DMF are added. The suspension is cooled to 10° C. and a solution of 1.55 g (10 mMol) 4,6-dichloropyrimidine in 25 ml DMF is added. The reaction mixture is stirred at room temperature for 14 h. The solvent is evaporated off and the mixture is partitioned between $H_2O$/EtOAc. After extraction, the aqueous phase is neutralized with a 1 N solution of HCl. The suspension is extracted with EtOAc, washed with $H_2O$ and brine, dried ($MgSO_4$) and concentrated to give a beige powder: $^1$H-NMR (DMSO-$d_6$): δ ppm 7.60 (s, 1H), 7.68 (dd, J=9.4, 2.3 Hz, 1H), 7.98 (d, J=2.3 Hz, 1H), 8.04 (d, J=5.5 Hz, 1H), 8.59 (d, J=5.9 Hz, 1H), 8.66 (s, 1H), 8.68 (s, 1H).

Step 23.2 6-(6-Chloro-pyrimidin-4-yloxy)-isoquinoline-1-carbonyl chloride

A solution of 870 μl (10.2 mMol) oxalyl chloride in 10 ml $CH_2Cl_2$ is added to an ice-cooled solution of 1.54 g (5.1 mMol) 6-(6-chloro-pyrimidin-4-yloxy)-isoquinoline-1-carboxylic acid and 10 μl DMF in 75 ml $CH_2Cl_2$. The reaction mixture is stirred at room temperature for 1 h. The solvent is then evaporated off under reduced pressure to afford the title compound as a brown solid, which is used directly without further purification.

Step 23.3: 6-(6-Chloro-pyrimidin-4-yloxy)-isoquinoline-1-carboxylic acid [5-tert-butyl-2-(4-methoxy-phenyl)-2H-pyrazol-3-yl]-amide 454.6 mg (1.42 mMol) 6-(6-Chloropyrimidin-4-yloxy)-isoquinoline-1-carbonyl chloride is dissolved in 10 ml $CH_2Cl_2$ and cooled to 0° C. At this temperature 0.46 ml (5.9 mMol) pyridine are added followed by 418.0 mg (1.7 mMol) 5-tert-butyl-2-(4-methoxy-phenyl)-2H-pyrazol-3-ylamine (Step 19.1). The reaction mixture is then allowed to warm to rt and stirred at ambient temperature for 1 h. It is worked up by addition of $H_2O$ and $CH_2Cl_2$. The organic layer is separated washed with brine and dried. After evaporation of the solvents the crude product is purified by chromatography (combi-flash: 40 g column, hexanes/EtOAc, gradient 0-50% EtOAc) to give the title compound as a yellow solid: m.p.: 156° C.; MS.

Example 24

6-(6-Acetylamino-pyrimidin-4-yloxy)-naphthalene-1-carboxylic acid [4-(4-methyl-piperazin-1-ylmethyl)-phenyl]-amide

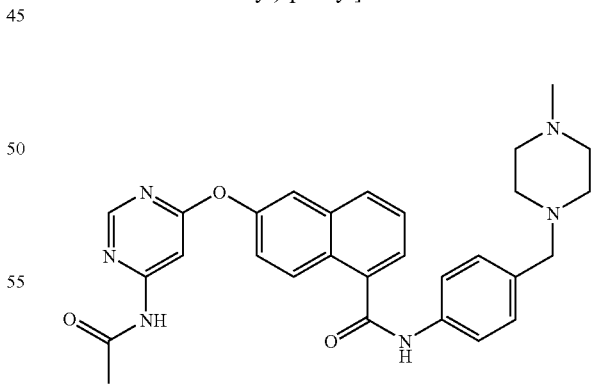

A mixture of 244 mg (0.5 mMol) 6-(6-chloro-pyrimidin-4-yloxy)-naphthalene-1-carboxylic acid [4-(4-methyl-piperazin-1-ylmethyl)-phenyl]-amide, 45 mg (0.75 mMol) acetamide, 18 mg (0.03 mMol) (9,9-dimethyl-9H-xanthene-4,5-diyl)bis[di-phenylphosphine] (=Xantphos), 9 mg (0.01 mMol) tris(dibenzylideneacetone)dipalladium and 228 mg (0.7 mMol) cesium carbonate in 2 ml dry dioxane is stirred under an argon atmosphere at 70° C. for 3 h. The cooled suspension is diluted with water, filtered (hyflo) and the residue is dissolved in EtOAc. The solvent is evaporated off under reduced pressure to afford the crude product which is purified by reversed phase medium pressure liquid chromatography (gradient 15%→50% $CH_3CN/H_2O$ containing 0.1% TFA) to afford, after neutralisation with sat. aq. $NaHCO_3$, the title compound as a beige powder: m.p.: 238-242° C.

The starting material is prepared as follows:

Step 24.1: 6-(6-Chloro-Pyrimidin-4-yloxy)-naphthalene-1-carboxylic acid [4-(4-methyl-piperazin-1-ylmethyl)-phenyl]-amide A solution of 2.2 mMol 6-(6-chloropyrimidin-4-yloxy)-naphthalene-1-carbonyl chloride (Step 19.3) in 15 ml $CH_2Cl_2$ is added to a stirred solution of 410 mg (2.0 mMol) 4-(4-methyl-piperazin-1-ylmethyl)-phenylamine and 680 µl (4.0 mMol) diisopropylethylamine in 15 ml $CH_2Cl_2$. After 30 min, the reaction mixture is poured into a mixture of $NaHCO_3$ and $CH_2Cl_2$. The aq. phase is separated off and extracted with $CH_2Cl_2$. The combined organic layers are washed with water and brine, dried ($Na_2SO_4$) and concentrated to give the crude product which is purified by column chromatography ($SiO_2$; $CH_2Cl_2/EtOH/NH_3$ 95:4.5:0.5) to afford the title compound as a yellow powder.

Example 25

6-(6-Acetylamino-pyrimidin-4-yloxy)-naphthalene-1-carboxylic acid [4-(1-methyl-Piperidin-4-ylmethyl)-3-trifluoromethyl-phenyl]-amide

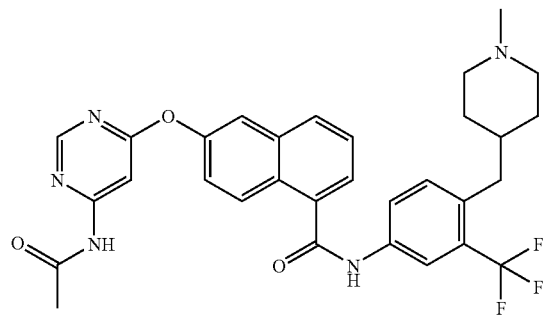

This compound can be obtained analogously to Ex. 24, utilising 4-(1-methyl-piperidin-4-ylmethyl)-3-trifluoromethyl-phenylamine in lieu of 4-(4-methyl-piperazin-1-ylmethyl)-phenylamine in Step 24.1: Beige powder; MS: $[M+1]^+$=578; TLC ($CH_2Cl_2/EtOH/NH_3$ 90:9:1): $R_f$=0.13.

The starting materials is made as follows:

Step 25.1: [4-(2,2,2-Trifluoro-acetylamino)-2-trifluoromethyl-benzyl]-phosphonic acid diethyl ester A mixture of 1.75 g (5 mMol) N-(4-bromomethyl-3-trifluoromethyl-phenyl)-2,2,2-trifluoro-acetamide (WO 2005/051366; Step 14.2) and 1.05 ml (6 mMol) triethylphosphite in 10 ml toluene is heated at 120° C. for 6 h. After cooling, the suspension is filtered and the crystalline solid washed with hexane to give the title compound as a colourless solid.

Step 25.2: 4-(1-Methyl-piperidin-4-ylidenemethyl)-3-trifluoromethyl-phenylamine 1.66 g (4.08 mMol) [4-(2,2,2-Trifluo-acetylamino)-2-trifluoromethyl-benzyl]-phosphonic acid diethyl ester are added portionwise to a suspension of 0.39 g (8.93 mMol) NaH in 50 ml THF. Then 0.51 ml (4.4 mMol) 1-methyl-4-piperidone are added to the suspension and it is stirred at rt for 14 h. Water is cautiously added to the reaction mixture and after 30 min stirring at rt, 5 ml of a 4 N NaOH solution are added and the solvent is evaporated off under reduced pressure. The mixture is then diluted with water and extracted twice with EtOAc. The combined organic layers are washed with water and brine, dried ($Na_2SO_4$). The solvent is evaporated off under reduced pressure to give the crude product which is purified by column chromatography ($SiO_2$; $CH_2Cl_2/EtOH/NH_3$ 95:4.5:0.5) to afford the title compound as a yellow crystalline solid.

Step 25.3: 4-(1-Methyl-piperidin-4-ylmethyl)-3-trifluoromethyl-phenylamine

A solution of 2.2 g (8.15 mMol) 4-(1-methyl-piperidin-4-ylidenemethyl)-3-trifluoromethyl-phenylamine in 50 ml EtOH is hydrogenated in the presence of PVC for 32 h at ambient temperature. The catalyst is then removed by filtration over hyflo and the solvent is evaporated off under reduced pressure to give the crude product which is purified by column chromatography ($SiO_2$; $CH_2Cl_2/EtOH/NH_3$ 95:4.5:0.5) to afford the title compound as a beige solid.

Example 26

6-(6-Acetylamino-pyrimidin-4-yloxy)-naphthalene-1-carboxylic acid [4-(1-methyl-piperidin-4-ylidenemethyl)-3-trifluoromethyl-phenyl]-amide

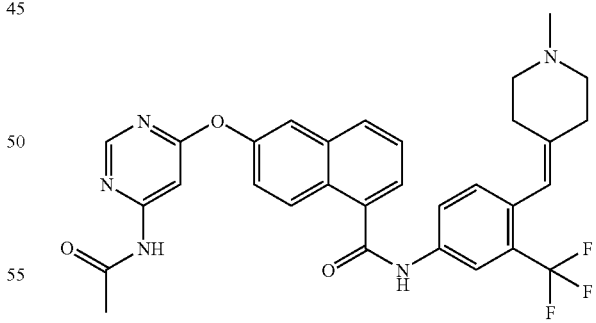

This compound can be obtained analogously to Ex. 24, utilising 4-(1-methyl-piperidin-4-ylidenemethyl)-3-trifluoromethyl-phenylamine (Step 25.2) in lieu of 4-(4-methyl-piperazin-1-ylmethyl)-phenylamine in Step 24.1: Beige powder; MS: $[M+1]^+$=576; TLC ($CH_2Cl_2/EtOH/NH_3$ 90:9:1): $R_f$=0.27.

Example 27

6-(6-Acetylamino-pyrimidin-4-yloxy)-naphthalene-1-carboxylic acid [4-(1-methyl-Piperidin-4-yloxy)-3-trifluoromethyl-phenyl]-amide

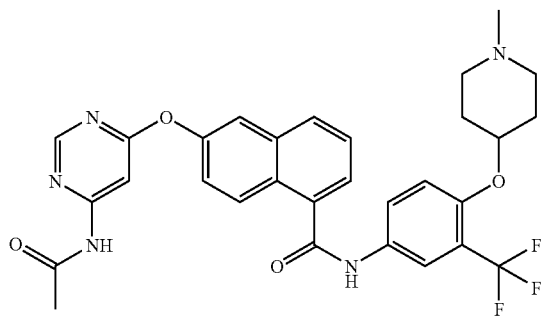

This compound can be obtained analogously to Ex. 24, utilising 4-(1-methyl-piperidin-4-yloxy)-3-trifluoromethyl-phenylamine in lieu of 4-(4-methyl-piperazin-1-ylmethyl)-phenylamine in Step 24.1:

Beige powder; MS: [M+1]$^+$=580; TLC (CH$_2$Cl$_2$/EtOH/NH$_3$ 90:9:1): R$_f$=0.14.

Example 28

(rac)-6-(6-Acetylamino-pyrimidin-4-yloxy)-naphthalene-1-carboxylic acid [4-(3-dimethylamino-pyrrolidin-1-yl)-3-trifluoromethyl-phenyl]-amide

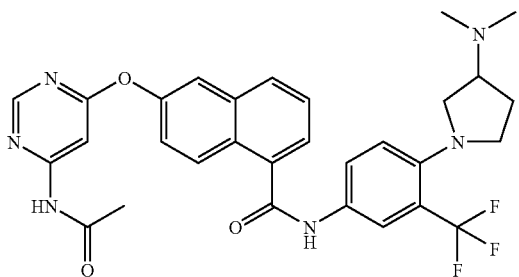

This compound can be obtained analogously to Ex. 24, utilising (rac)-[1-(4-amino-2-trifluoromethyl-phenyl)-pyrrolidin-3-yl]-dimethyl-amine in lieu of 4-(4-methyl-piperazin-1-ylmethyl)-phenylamine in Step 24.1: Beige powder; MS: [M+1]$^+$=579; TLC (CH$_2$Cl$_2$/EtOH/NH$_3$ 90:9:1): R$_f$=0.25.

Example 29

6-(6-Acetylamino-pyrimidin-4-yloxy)-naphthalene-1-carboxylic acid [4-(9-methyl-3,9-diaza-bicyclo[3.3.1]non-3-ylmethyl)-3-trifluoromethyl-phenyl]-amide

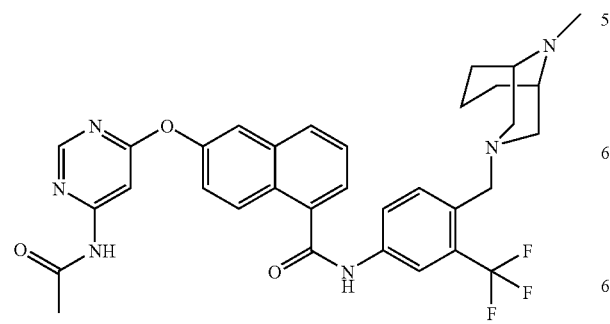

This compound can be obtained analogously to Ex. 24, utilising 4-(9-methyl-3,9-diazabicyclo[3.3.1]non-3-ylmethyl)-3-trifluoromethyl-phenylamine in lieu of 4-(4-methyl-piperazin-1-ylmethyl)-phenylamine in Step 24.1: Beige powder; MS: [M+1]$^+$=619; TLC (CH$_2$Cl$_2$/EtOH/NH$_3$ 90:9:1): R$_f$=0.11.

The starting materials is made as follows:

Step 29.1: 4-(9-Methyl-3,9-diaza-bicyclo[3.3.1]non-3-ylmethyl)-3-trifluoromethyl-phenylamine A solution of 296 mg (0.85 mMol) N-(4-bromomethyl-3-trifluoromethyl-phenyl)-2,2,2-trifluoro-acetamide (WO 2005/051366; Step 14.2) in 5 ml of CH$_3$CN is added at 5° C. within 30 min to a solution of 213 mg (1.00 mMol) 9-methyl-3,9-diaza-bicyclo[3.3.1]nonane dihydrochloride (synthesized according to Barnes, Roderick A. et al.: *J. Am. Chem. Soc.* 1953, 75, 975) and 0.7 ml (4 mMol) ethyldiisopropylamine in 10 ml CH$_3$CN. After 1.5 h at 5-10° C., the solvent is evaporated off under reduced pressure. The residue is dissolved in EtOAc and washed with NaHCO$_3$. The aq. phase is re-extracted with EtOAc and the combined organics are washed with water, brine and dried over Na$_2$SO$_4$. The solvent is evaporated off under reduced pressure and the residue is dissolved in a mixture of 10 ml MeOH and 2 ml of a 2 M NaOH solution and stirred at 50° C. for 3 h. The MeOH is evaporated off under reduced pressure, the mixture is diluted with water and extracted 3 times with EtOAc. The combined organics are washed with water and brine and dried (Na$_2$SO$_4$). The solvent is evaporated off under reduced pressure to give the crude product which is purified by column chromatography (SiO$_2$; CH$_2$Cl$_2$/EtOH/NH$_3$ 95:4.5:0.5) to afford the title compound as a crystalline solid.

Example 30

6-(6-Acetylamino-pyrimidin-4-yloxy)-naphthalene-1-carboxylic acid [4-(4-cyclopropyl-piperazin-1-ylmethyl)-3-trifluoromethyl-phenyl]-amide

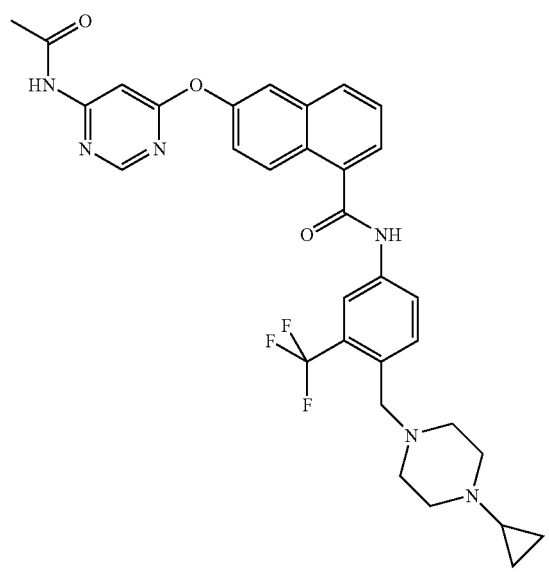

This compound can be obtained analogously to Ex. 24, utilising 4-(4-cyclopropyl-piperazin-1-ylmethyl)-3-trifluoromethyl-phenylamine in lieu of 4-(4-methyl-piperazin-1-yl-methyl)-phenylamine in Step 24.1: Beige powder; MS: [M+1]$^+$=605; TLC (CH$_2$Cl$_2$/EtOH/NH$_3$ 95:4.5:0.5): R$_f$=0.12.

Example 31

6-(6-Acetylamino-pyrimidin-4-yloxy)-naphthalene-1-carboxylic acid [4-(1,1-dioxido-4-thiomorpholinyl)-3-trifluoromethyl-phenyl]-amide

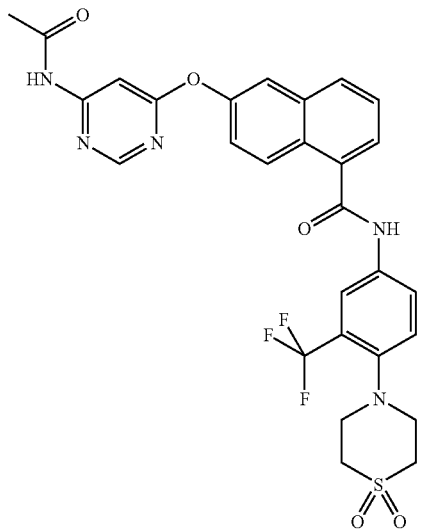

This compound can be obtained analogously to Ex. 24, utilising 4-(1,1-dioxido-4-thiomorpholinyl)-3-trifluoromethyl-phenylamine in lieu of 4-(4-methyl-piperazin-1-ylmethyl)-phenylamine, as a crystalline solid: m.p.: 280-287° C.

Example 32

6-(6-Acetylamino-pyrimidin-4-yloxy)-naphthalene-1-carboxylic acid [4-[[(+/−)-3-(dimethylamino)-1-pyrrolidinyl]methyl]-3-(trifluoromethyl)phenyl]-amide

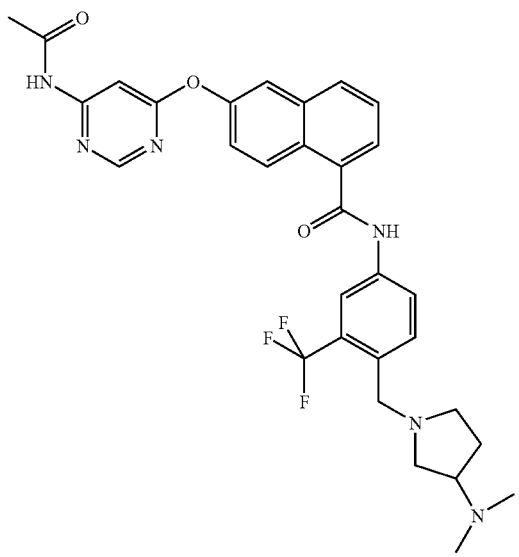

This compound can be obtained analogously to Ex. 24, utilising rac. 1-[[5-amino-2-(trifluoromethyl)phenyl]methyl]-N,N-dimethyl-3-pyrrolidinamine, in lieu of 4-(4-methyl-piperazin-1-ylmethyl)-phenylamine in Step 24.1, as a solid.

Example 33

6-(6-Acetylamino-pyrimidin-4-yloxy)-naphthalene-1-carboxylic acid [3-(4-methyl-1-piperazinyl)-5-(trifluoromethyl)phenyl]-amide

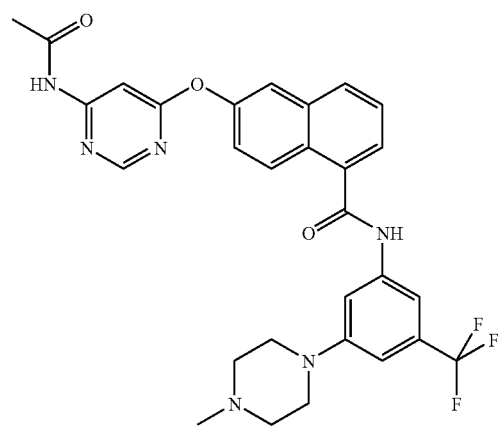

This compound can be obtained analogously to Ex. 24, utilising 3-(4-methyl-1-piperazinyl)-5-(trifluoromethyl)-benzenamine, in lieu of 4-(4-methyl-piperazin-1-ylmethyl)-phenylamine in Step 24.1, as a solid.

Example 34

6-(6-Acetylamino-pyrimidin-4-yloxy-naphthalene-1-carboxylic acid [3-(4-phenylmethyl-1-piperazinyl)-5-(trifluoromethyl)phenyl]-amide

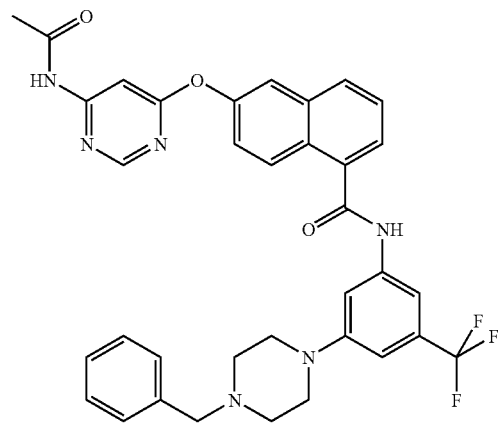

This compound can be obtained analogously to Ex. 24, utilising 3-(4-phenylmethyl-1-piperazinyl)-5-(trifluoromethyl)-benzenamine, in lieu of 4-(4-methyl-piperazin-1-ylmethyl)-phenylamine in Step 24.1, as a solid.

Example 35

[(3S)-1-[4-[[[6-(6-Acetylamino-pyrimidin-4-yloxy)-naphthalen-1-yl]carbonyl-]-amino]-2-(trifluoromethyl)phenyl]-3-piperidinyl]-carbamic acid, 1,1-dimethylethyl ester

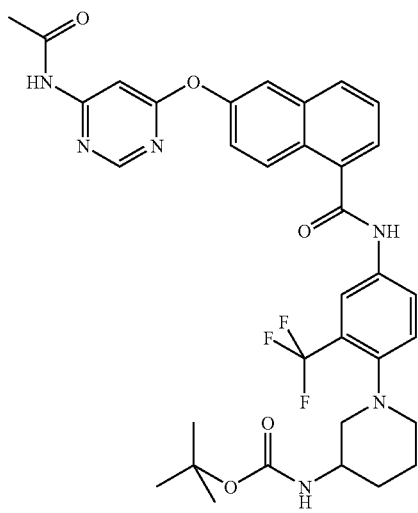

This compound can be obtained analogously to Ex. 24, utilizing [(3S)-1-[4-amino-2-(trifluoromethyl)phenyl]-3-piperidinyl]-carbamic acid, 1,1-dimethylethyl ester in lieu of 4-(4-methyl-piperazin-1-ylmethyl)-phenylamine in Step 24.1, as a an orange solid.

Example 36

[(3R)-1-[4-[[[6-(6-Acetylamino-pyrimidin-4-yloxy)-naphthalen-1 yl]carbonyl-]-amino]-2-(trifluoromethyl)phenyl]-3-piperidinyl]-carbamic acid, 1,1-dimethylethyl ester

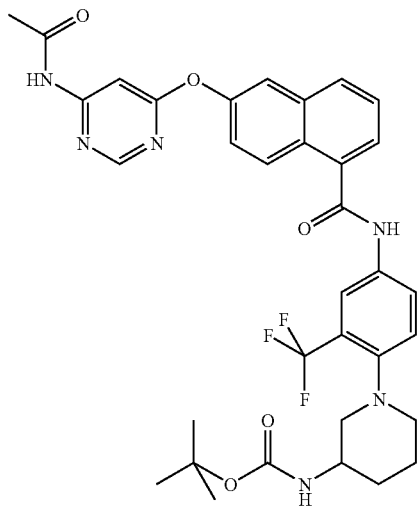

This compound can be obtained analogously to Ex. 24, utilizing [(3R)-1-[4-amino-2-(trifluoromethyl)phenyl]-3-piperidinyl]-carbamic acid, 1,1-dimethylethyl ester in lieu of 4-(4-methyl-piperazin-1-ylmethyl)-phenylamine in Step 24.1, as an orange solid.

Example 37

6-(6-Acetylamino-pyrimidin-4-yloxy)-naphthalene-1-carboxylic acid [4-[(3S)-3-amino-1-piperidinyl]-3-trifluoromethyl-phenyl]-amide

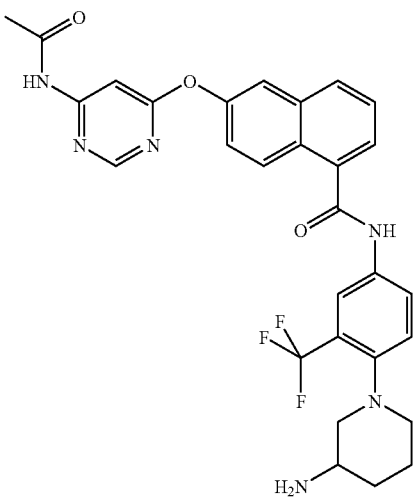

A solution of 2.3 ml hydrogen chloride (4 M in dioxane) is added to a stirred solution of 0.24 g (0.38 mmol) [(3S)-1-[4-[[[6-(6-acetylamino-pyrimidin-4-yloxy)-naphthalen-1-yl]carbonyl-]-amino]-2-(trifluoromethyl)phenyl]-3-piperidinyl]-carbamic acid, 1,1-dimethylethyl ester (Ex. 35) in 2.3 ml dioxan at room temperature. After 90 min, the mixture is poured into an excess of saturated aqueous NaHCO$_3$. The crude product is filtered and purified by chromatography (SiO$_2$, CH$_2$Cl$_2$/EtOH/NH$_3$ 90:9:1) to afford the title compound as a beige solid: m.p.: 218-228° C.

Example 38

6-(6-Acetylamino-pyrimidin-4-yloxy)-naphthalene-1-carboxylic acid [4-[(3R)-3-amino-1-piperidinyl]-3-trifluoromethyl-phenyl]-amide

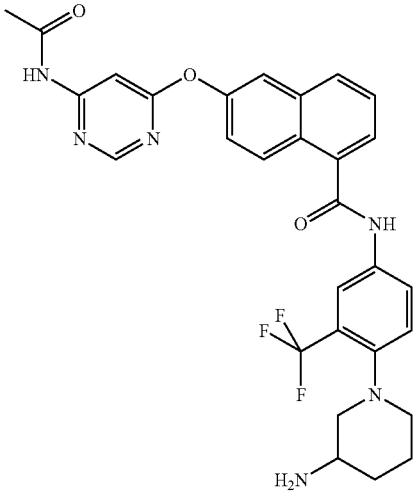

This compound can be obtained analogously to Ex. 37, utilizing [(3S)-1-[4-[[[6-(6-acetylamino-pyrimidin-4-yloxy)-naphthalen-1-yl]carbonyl-]-amino]-2-(trifluoromethyl)phenyl]-3-piperidinyl]-carbamic acid, 1,1-dimethylethyl ester (Ex. 36) in lieu of [(3R)-1-[4-[[[6-(6-acetylamino-pyrimidin-4-yloxy)-naphthalen-1-yl]carbonyl-]-amino]-2-(trifluoromethyl)phenyl]-3-piperidinyl]-carbamic acid, 1,1-dimethylethyl ester, to afford the title compound as a colourless solid: m.p.: 219-226° C.

Example 39

6-[6-(Cyclopropylcarbonyl)amino-pyrimidin-4-yloxy]-naphthalene-1-carboxylic acid [4-(1,1-di-oxido-4-thiomorpholinyl)-3-trifluoromethyl-phenyl]-amide

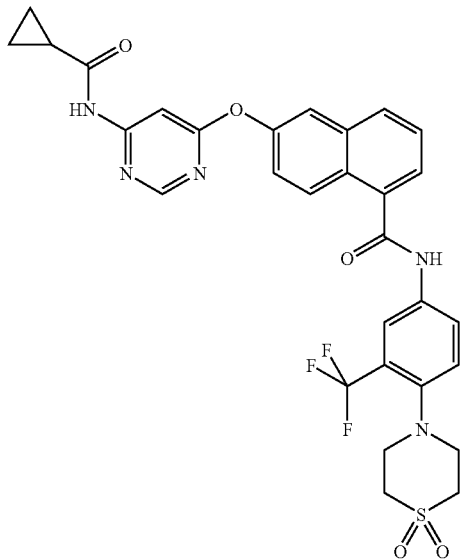

This compound can be obtained analogously to Ex. 31, but utilizing cyclopropanecarboxamide in lieu of acetamide, to afford the title compound as a beige solid: m.p.: 195-205° C.

Example 40

6-[6-(Cyclopropylcarbonyl)amino-pyrimidin-4-yloxy]-naphthalene-1-carboxylic acid [4-[(3R)-3-amino-1-piperidinyl]-3-trifluoromethylphenyl]-amide

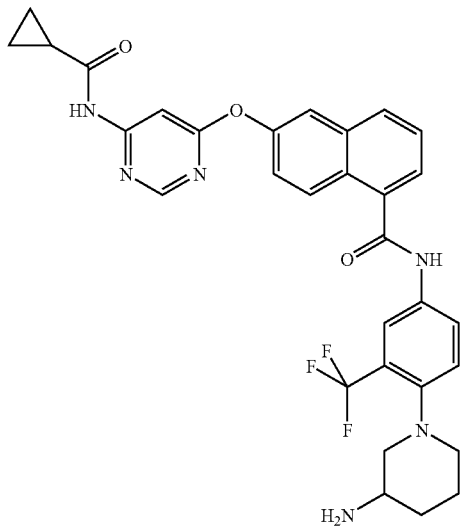

This compound can be obtained analogously to Ex. 38, but utilizing cyclopropanecarboxamide in lieu of acetamide, to afford the title compound as a colourless solid.

Example 41

6-[[6-[(Cyclopropylcarbonyl)amino]-4-pyrimidinyl]oxy]-N-[4-[(4-methyl-1-piperazinyl)methyl]-3-(trifluoromethyl)phenyl]-1-naphthalenecarboxamide,

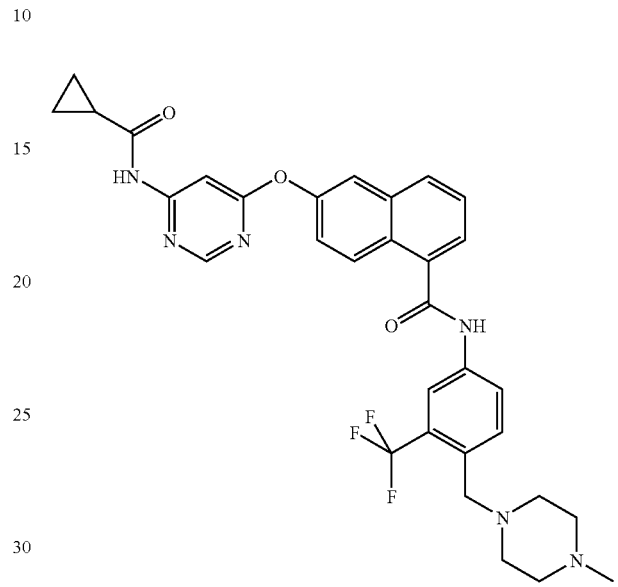

This compound can be obtained analogously to Ex. 24, but utilising cyclopropanecarboxamide in lieu of acetamide and 4-[(4-methyl-1-piperazinyl)methyl]-3-(trifluoromethyl)benzenamine in lieu of 4-(4-methyl-piperazin-1-ylmethyl)phenylamine, to afford the title compound as a colourless solid.

Example 42

Dry-Filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverised and forced through a sieve of 0.6 mm mesh size. 0.33 g portions of the mixture are introduced into gelatin capsules using a capsule-filling machine.

Example 43

Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 litre |
| Tween 80 | 1 litre |

Preparation process: The active ingredient is pulverised and suspended in PEG 400 (polyethylene glycol having an $M_r$ of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulveriser to a particle size of approx. from 1 to 3 μm. 0.43 g portions of the mixture are then introduced into soft gelatin capsules using a capsule-filling machine.

The invention claimed is:

1. A compound of the formula IA

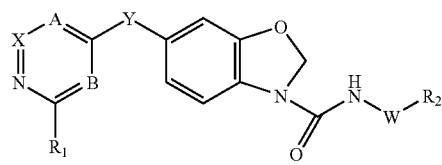

(IA)

wherein $R_1$ is hydroxyl, lower-alkoxy-lower alkyl, lower alkylsulfonylamino, amino-lower alkylamino, N-mono- or N,N-di-(lower alkyl)amino-lower alkylamino, N-mono- or N,N-di-(lower alkyl)amino-carbonyl-amino-, piperazinyl-lower alkylamino, N-lower alkylpiperazinyl-lower alkylamino, hydrazine, mono- di- or tri-(lower alkyl)-substituted hydrazine, $R_2$ is phenyl substituted by a substituent selected from the group consisting of phenoxy, piperazinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl; or is phenyl substituted by one or two moieties independently selected from lower alkyl, $C_3$-$C_8$-cycloalkyl, halo, halo-lower alkyl, halo-lower alkoxy, or by lower alkoxy, or is 2H-pyrazolyl substituted by halophenyl and lower alkyl;

or wherein $R_1$ is halo, amino, lower alkylamino, lower alkanoylamino, lower alkoxycarbonylamino, $C_{3-8}$cycloalkylcarbonyl amino or hydroxyl-lower alkyl and $R_2$ is phenyl substituted by a substituent selected from the group consisting of phenoxy, piperazinyl-lower alkyl, lower-alkylpiperazinyl, lower-alkylpiperazinyl-lower alkyl, $C_3$-$C_8$-cycloalkyl-piperazinyl-lower alkyl, phenyl lower-alkyl piperaziyl, piperidinyl-lower alkyl, lower-alkylpiperidinyl-lower alkyl, amino piperidinyl, lower alkoxycarbonylamino piperidinyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl, N-mono- or N,N-di-lower alkylaminopyrrolidinyl lower alkyl, 1,1-dioxido-4-thiomorpholinyl, and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy; or is 2H-pyrazolyl that is unsubstituted or substituted by lower alkyl and by one or two moieties independently selected from lower alkoxyphenyl and lower alkoxyphenylphenyl;

A, B and X are independently selected from $C(R_3)$ or N, with the proviso that X is $C(R_3)$, one of A and B is N and the other is $C(R_3)$;

$R_3$ is lower alkyl, halo or hydrogen;

Y is O, S, S(O), $S(O)_2$, $CH_2$ or $CH_2$—$CH_2$; and

W is absent or is lower alkylene;

a tautomer and/or a salt thereof.

2. A compound of the formula IA according to claim 1 wherein $R_1$ is hydroxyl, lower-alkoxy-lower alkyl, lower alkylsulfonylamino, amino-lower alkylamino, N-mono- or N,N-di-(lower alkyl)amino-lower alkylamino, N-mono- or N,N-di-(lower alkyl)amino-carbonyl-amino, piperazinyl-lower alkylamino, N-lower alkylpiperazinyl-lower alkylamino, hydrazine, mono-, di- or tri-(lower alkyl)-substituted hydrazine;

$R_2$ is phenyl substituted by a substituent selected from the group consisting of phenoxy, piperazinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, amino-pyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

and A, B, X, Y, W and $R_2$ are as defined in claim 1;

a tautomer and/or a salt thereof.

3. A compound of the formula IA according to claim 1 wherein $R_1$ is hydroxyl, lower alkoxy-lower alkyl, amino-lower alkylamino, or N-mono- or N,N-di-(lower alkyl)amino-lower alkylamino, and $R_2$ is phenyl substituted by one or two moieties independently selected from lower alkyl, $C_3$-$C_8$-cycloalkyl, halo, halo-lower alkyl, halo-lower alkoxy or by lower alkoxy, or is 2H-pyrazolyl substituted by halophenyl or lower alkyl;

while the other symbols A, B, X, Y and W are as defined for formula IA in claim 1;

a tautomer and/or a salt thereof.

4. A compound of the formula IA according to claim 1 wherein $R_1$ is halo, piperazinyl-lower alkylamino or N-lower alkylpiperazinyl-lower alkylamino, and $R_2$ is 2H-pyrazolyl substituted by halophenyl and lower alkyl;

While the other symbols A, B, X, Y and W are as defined claim 1;
a tautomer and/or a salt thereof.

5. A compound of the formula IA according to claim 1 wherein $R_1$ is halo, amino, lower alkylamino, lower alkanoylamino, lower alkoxycarbonylamino or hydroxyl-lower alkyl and $R_2$ is phenyl substituted by a substituent selected from the group consisting of phenoxy, piperzinyl-lower alkyl, lower-alkylpiperazinyl-lower alkyl, $C_3$-$C_8$-cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, aminopyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

while the other symbols A, B, X, Y and W are as defined for formula IA in claim 1;
a tautomer and/or a salt thereof.

6. A compound of the formula IA according to claim 1 wherein $R_1$ is hydroxyl-lower alkyl or lower alkoxy-lower alkyl;

$R_2$ is phenyl that is substituted by one or two moieties independently selected from the group consisting of lower alkyl, $C_3$-$C_8$cycloalkyl, halo, halo lower alkyl, lower alkoxy, phenoxy, piperazinyl-lower alkyl, lower-alkylpiperazinyl-lower alkyl and halo-lower alkoxy, and W is as defined in claim 1,
a tautomer and/or a salt thereof.

7. A compound of the formula IA according to claim 1 wherein $R_1$ is halo, amino, lower alkylamino, lower alkanoylamino or lower alkoxycarbonylamino and $R_2$ is phenyl that is substituted by two moieties independently selected from halo, halo-lower alkyl, piperzinyl-lower alkyl and lower-alkyl-piperazinyl-lower alkyl, one of A, B and X is N and the others are $CH_2$, and
Y is $CH_2$;
while W is as defined in claim 1,
a tautomer and/or a salt thereof.

8. A compound of the formula IA according to claim 1 wherein $R_1$ is lower alkoxy-lower alkyl, $R_2$ is phenyl substituted by a substituent selected from the group consisting of phenoxy, piperazinyl-lower alkyl, lower-alkylpiperazinyl-lower alkyl, $C_3$-$C_8$cycloalkyl-piperazinyl-lower alkyl, piperidinyl-lower alkyl, lower-alkylpiperidinyl-lower alkyl, piperidinyliden-lower alkyl, lower-alkylpiperidinyliden-lower alkyl, piperidinyloxy, lower alkylpiperidinyloxy, pyrrolidinyl, aminopyrrolidinyl, N-mono- or N,N-di-lower alkylaminopyrrolidinyl and 9-lower alkyl-3,9-diazabicyclo[3.3.1]non-3-yl-lower alkyl, or in all cases by one of the mentioned substituents and in addition by a moiety selected from lower alkyl, $C_3$-$C_8$-cycloalkyl, halo, halo-lower alkyl, halo-lower alkoxy and lower alkoxy;

or is 2H-pyrazolyl that is unsubstituted or substituted by lower alkyl and by one or two moieties independently selected from lower alkoxyphenyl and lower alkoxyphenylphenyl;

or is phenyl substituted by one or two moieties independently selected from lower alkyl, $C_3$-$C_8$-cycloalkyl, halo, halo-lower alkyl, halo-lower alkoxy or by lower alkoxy, or is 2H-pyrazolyl substituted by halophenyl and lower alkyl;

or is 2H-pyrazolyl substituted by halophenyl and lower alkyl;

and symbols A, B, X, Y and W are as defined for formula IA in claim 1;
a tautomer and/or a salt thereof.

9. A compound of the formula IA according to claim 1 wherein $R_1$ is lower alkoxycarbonyl or lower alkanoyl;
$R_2$ is phenyl substituted in 4-position by halo and in 3-position by halo-lower alkyl;
X is CH;
B is N;
Y is O and
W is as defined in claim 1,
A tautomer thereof and/or a pharmaceutically acceptable salt thereof.

10. A compound of the formula IA according to claim 1 wherein W is absent.

11. A pharmaceutical preparation comprising a compound of the formula IA, a tautomer and/or a salt thereof according to claim 1 and at least one pharmaceutically acceptable carrier material.

12. A compound of the formula IA according to claim 1, selected from the group of compounds consisting of
6-(2-chloro-pyrimidin-4-yloxy)-benzooxazole-3-carboxylic acid (4-chloro-3-trifluoromethyl-phenyl)-amide;
6-(2-methylamino-pyrimidin-4-yloxy)benzooxazole-3-carboxylic acid (4-chloro-3-trifluoromethyl-phenyl)-amide;
a tautomer thereof and/or a pharmaceutically acceptable salt thereof.

* * * * *